United States Patent
Eckert et al.

(10) Patent No.: US 11,466,098 B2
(45) Date of Patent: Oct. 11, 2022

(54) BINDING AGENT AND ASSAY FOR PIVKA

(71) Applicant: Roche Diagnostics Operations, Inc., Indianapolis, IN (US)

(72) Inventors: Bernhard Eckert, Weilheim (DE); Michael Gerg, Munich (DE); Johann Karl, Peissenberg (DE); Martin Kaufmann, Weilheim (DE); Julia Riedlinger, Ottobrunn (DE); Magdelena Swiatek-de Lange, Penzberg (DE); Lars Hillringhaus, Koenigsdorf-Schoerain (DE); Klaus Hirzel, Baierbrunn (DE); Marcus-Rene Lisy, Geretsried (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 155 days.

(21) Appl. No.: 16/740,778

(22) Filed: Jan. 13, 2020

(65) Prior Publication Data
US 2020/0140569 A1 May 7, 2020

Related U.S. Application Data

(63) Continuation of application No. PCT/EP2018/068871, filed on Jul. 12, 2018.

(30) Foreign Application Priority Data

Jul. 13, 2017 (EP) .................................... 17181242

(51) Int. Cl.
*C07K 16/36* (2006.01)
*G01N 33/574* (2006.01)
*G01N 33/86* (2006.01)

(52) U.S. Cl.
CPC ....... *C07K 16/36* (2013.01); *G01N 33/57438* (2013.01); *G01N 33/86* (2013.01); *C07K 2317/565* (2013.01); *G01N 2333/745* (2013.01)

(58) Field of Classification Search
None
See application file for complete search history.

(56) References Cited

U.S. PATENT DOCUMENTS

| | | | |
|---|---|---|---|
| 5,316,757 A | 5/1994 | Sherry et al. |
| 5,342,606 A | 8/1994 | Sherry et al. |
| 5,385,893 A | 1/1995 | Kiefer |
| 5,403,484 A | 4/1995 | Ladner et al. |
| 5,428,139 A | 6/1995 | Kiefer et al. |
| 5,428,155 A | 6/1995 | Sherry et al. |
| 5,462,725 A | 10/1995 | Kiefer et al. |
| 5,480,990 A | 1/1996 | Kiefer et al. |
| 5,582,981 A | 12/1996 | Toole et al. |
| 5,739,294 A | 4/1998 | Kiefer et al. |
| 5,750,660 A | 5/1998 | Kiefer et al. |
| 5,834,456 A | 11/1998 | Kiefer et al. |
| 5,877,397 A | 3/1999 | Lonberg et al. |
| 5,885,793 A | 3/1999 | Griffiths et al. |
| 5,969,108 A | 10/1999 | McCafferty et al. |
| 10,539,559 B2 | 1/2020 | Yamaguchi et al. |
| 2011/0111856 A1 | 5/2011 | White et al. |
| 2014/0024050 A1 | 1/2014 | Yoshimura et al. |

FOREIGN PATENT DOCUMENTS

| | | |
|---|---|---|
| JP | 2013541936 | 11/2013 |
| JP | 2014035278 | 2/2014 |
| WO | 1994/020627 A1 | 9/1994 |
| WO | 2012/002345 A1 | 1/2012 |
| WO | 2012/107419 A1 | 8/2012 |
| WO | 2012018476 A1 | 9/2012 |

OTHER PUBLICATIONS

Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Kanyavuz et al., Nat Rev Immunol. Jun. 2019;19(6):355-368. doi: 10.1038/S41577-019-0126-7.*
Lescar, et al. Journal of Biological Chemistry 270.30 (1995): 18067-18076.*
Ulrich et al., J Biol Chem. Jul. 15, 1988;263(20):9697-702. PMID: 3133366.*
Bae et al., BMC Cancer. Oct. 10, 2011;11:435. doi: 10.1186/1471-2407-11-435. PMID: 21985636.*
Stryer, L., Biochemistry, 4th edition, W. H. Freeman and Company, 1995, pp. 18-23.*
Lee, Jung Ee et al., Diagnostic Efficiency of Plasma PIVKA-II Levels in Hepatocellular Carcinoma, Korean Journal of Clinical Pathology, 1997, pp. 395-404, vol. 17, No. 3.
Motohara, Kunihiko et al., Detection of Vitamin K Deficiency by Use of an Enzyme-Linked Immunosorbent Assay for Circulating Abnormal Prothrombin, Pediatric Research, 1985, pp. 354-357, vol. 19, No. 4.
Altschul, Stephen F. et al., Gapped BLAST and PSI-BLAST: a new generation of protein database search programs, Nucleic Acids Research, 1997, pp. 3389-3402, vol. 25, No. 17.
Bajaj, S. Paul et al., Decarboxylation of γ-Carboxyglutamic Acid Residues in Human Prothrombin, The Journal of Biological Chemistry, 1982, pp. 3726-3731, vol. 287, No. 7.

(Continued)

*Primary Examiner* — Michael Szperka
(74) *Attorney, Agent, or Firm* — Stinson LLP

(57) ABSTRACT

The present disclosure relates to specific binding agents binding to different PIVKA-II forms as compared to antibodies known so far in the art. The present disclosure also relates to methods of using the specific binding agents to detect the presence of PIVKA-II.

14 Claims, 4 Drawing Sheets
Specification includes a Sequence Listing.

(56) References Cited

OTHER PUBLICATIONS

Baldi, Lucia et al., Recombinant protein production by large-scale transient gene expression in mammalian cells: state of the art and future perspectives, Biotechnology Letters, 2007, pp. 677-684, vol. 29.
Baldi, Lucia et al., Transient Gene Expression in Suspension HEK-293 Cells: Application to Large-Scale Protein Production, Biotechnology Progress, 2005, pp. 148-153, vol. 21.
Blend, Michael J. et al., Labeling anti-HER2/neu Monoclonal Antibodies with 111In and 90Y Using a Bifunctional DTPA Chelating Agent, Cancer Biotherapy & Radiopharmaceuticals, 2003, pp. 355-363, vol. 18, No. 3.
Borowski, Marianne et al., Metal and Phospholipid Binding Properties of Partially Carboxylated Human Prothrombin Variants, The Journal of Biological Chemistry, 1985, pp. 9258-9264, vol. 260, No. 16.
Borowski, Marianne et al., Prothrombin Requires Two Sequential Metal-dependent Conformational Transitions to Bind Phospholipid Conformation-Specific Antibodies Directed Against the Phospholipid-Binding Site on Prothrombin, The Journal of Biological Chemistry, 1986, pp. 14969-14975, vol. 261, No. 32.
Briggs, Mark S. J. et al., Synthesis of functionalised fluorescent dyes and their coupling to amines and amino acids, Journal of the American Chemical Society, Perkin Trans. 1, 1997, pp. 1051-1058.
Browne, Susan M. and Al-Rubeai, Mohamed, Selection methods for high-producing mammalian cell lines, Trends in Biotechnology, 2007, pp. 425-432, vol. 25, No. 9.
Camera, L. et al., Evaluation of a new DTPA-derivative chelator: comparative biodistribution and imaging studies of 111In-labeled B3 monoclonal antibody in athymic mice bearing human epidermoid carcinoma xenografts, Nuclear Medicine and Biology, 1994, pp. 955-962, Abstract only, vol. 21.
Camera, Luigi et al., Comparative biodistribution of indium- and yttrium-labeled B3 monoclonal antibody conjugated to either 2-(p-SCN-Bz)-6-methyl-DTPA (1B4M-DTPA) or 2-(p-SCN-Bz)-1,4,7,10-tetraazacyclododecane tetraacetic acid (2B-DOTA), European Journal of Nuclear Medicine, 1994, pp. 640-646, vol. 21.
Denardo, Gerald L. et al., Comparison of 1,4,7,10-Tetraazacyclododecane-N,N',N'',N'''-tetraacetic acid (DOTA)-Peptide-ChL6, a Novel Immunoconjugate with Catabolizable Linker, to 2-Iminothiolane-2-[p-(Bromoacetamido)benzyl]-DOTA-ChL6 in Breast Cancer Xenografts, Clinical Cancer Research, 1998, pp. 2483-2490, vol. 4.
Dodeigne, C. et al., Chemiluminescence as diagnostic tool. A review, Talanta, 2000, pp. 415-439, vol. 51.
Dyson, Michael R. et al., Production of soluble mammalian proteins in *Escherichia coli*: identification of protein features that correlate with successful expression, BMC Biotechnology, 2004, 18 pp., vol. 4, No. 32.
Fujiyama, S. et al., Clinical evaluation of plasma abnormal prothrombin (PIVKA-II) in patients with hepatocellular carcinoma, Hepatogastroenterology, 1986, pp. 201-205, Abstract only, vol. 33, No. 5.
Girard, Philippe et al., 100-liter transient transfection, Cytotechnology, 2002, pp. 15-21, vol. 38.
Goldsmith, George H., Jr. et al., Studies on a family with combined functional deficiencies of vitamin K-dependent coagulation factors, The Journal of Clinical Investigation, 1982, pp. 1253-1260, vol. 69, No. 6.
Hartman, Standish C. and Mulligan, Richard C., Two dominant-acting selectable markers for gene transfer studies in mammalian cells, Proceedings of the National Academy of Sciences USA, 1988, pp. 8047-8051, vol. 85.
Henikoff, Steven and Henikoff, Jorja G., Amino acid substitution matrices from protein blocks, Proceedings of the National Academy of Sciences USA, 1992, pp. 10915-10919, vol. 89.

Herrera-Estrella, L. et al., Chimeric genes as dominant selectable markers in plant cells, The EMBO Journal, 1983, pp. 987-995, vol. 2, No. 6.
Hnatowich, D.J. et al., The Preparation of DTPA-Coupled Antibodies Radiolabeled with Metallic Radionuclides: an Improved Method, Journal of Immunological Methods, 1983, pp. 147-157, vol. 65.
International Search Report dated Oct. 4, 2018, in Application No. PCT/EP2018/068871.
Izard, M. E. et al., An Improved Method for Labeling Monoclonal Antibodies with Samarium-153: Use of the Bifunctional Chelate 2-(p-Isothiocyanatobenzyl)-6-methyldiethylenetriaminepentaacetic Acid, Bioconjugate Chemistry, 1992, pp. 346-350, vol. 3.
Jayasena, Sumedha D., Aptamers: An Emerging Class of Molecules That Rival Antibodies in Diagnostics, Clinical Chemistry, 1999, pp. 1628-1650, vol. 45, No. 9.
Kinukawa, Hideki et al., Epitope characterization of an anti-PIVKA-II antibody and evaluation of a fully automated chemiluminescent immunoassay for PIVKA-II, Clinical Biochemistry, 2015, pp. 1120-1125, vol. 48, No. 16-17.
Klug, Stefanie J. and Famulok, Michael, All you wanted to know about SELEX, Molecular Biology Reports, 1994, pp. 97-107, vol. 20.
Klußmann, Sven et al., Mirror-image RNA that binds D-adenosine, Nature Biotechnology, 1996, pp. 1112-1115, vol. 14.
Kobayashi, Hisataka et al., Evaluation of the in Vivo Biodistribution of Indium-111 and Yttrium-88 labeled Dendrimer-1B4M-DTPA and Its Conjugation with Anti-Tac Monoclonal Antibody, Bioconjugate Chemistry, 1999, pp. 103-111, vol. 10.
Kobayashi, Hisataka et al., Evaluation of the in Vivo Biodistribution of Yttrium-Labeled Isomers of CHX-DTPA-Conjugated Monoclonal Antibodies, Journal of Nuclear Medicine, 1998, pp. 829-836, vol. 39.
Kukis, David L. et al., Optimized Conditions for Chelation of Yttrium-90-DOTA Immunoconjugates, Journal of Nuclear Medicine, 1998, pp. 2105-2110, vol. 39.
Lee, Fook-Thean et al., Specific Localization, Gamma Camera Imaging, and Intracellular Trafficking of Radiolabelled Chimeric Anti-GD3 Ganglioside Monoclonal Antibody KM871 in SK-MEL-28 Melanoma Xenografts, Cancer Research, 2001, pp. 4474-4482, vol. 61.
Liebman, Howard A. et al., Des-γ-Carboxy (Abnormal) Prothrombin as a Serum Marker of Primary Hepatocellular Carcinoma, The New England Journal of Medicine, 1984, pp. 1427-1431, Abstract, vol. 310, No. 22.
Lim, Tae Seop et al., Combined use of AFP, PIVKA-II, and AFP-L3 as tumor markers enhances diagnostic accuracy for hepatocellular carcinoma in cirrhotic patients, Scandinavian Journal of Gastroenterology, 2015, pp. 344-353, vol. 51, No. 3.
Mardirossian, G. et al., The stability in liver homogenates of indium-111 and yttrium-90 attached to antibody via two popular chelators, Nuclear Medicine and Biology, 1993, pp. 65-74, vol. 20, No. 1.
Marrero, Jorge A. et al., Des-Gamma Carboxyprothrombin Can Differentiate Hepatocellular Carcinoma From Nonmalignant Chronic Liver Disease in American Patients, Hepatology, 2003, pp. 1114-1121, vol. 37.
Marsh, J. Lawrence et al., The pIC plasmid and phage vectors with versatile cloning sites for recombinant selection by insertional inactivation, Gene, 1984, pp. 481-485, vol. 32.
Matasci, Mattia et al., Recombinant therapeutic protein production in cultivated mammalian cells: current status and future prospects, Drug Discovery Today: Technologies, 2008, pp. e37-e42, vol. 5, No. 2-3.
Meares, C F. et al., Macrocyclic chelates of radiometals for diagnosis and therapy, British Journal of Cancer, 1990, pp. 21-26, vol. 62, Supp X.
Meares, Claude F. et al., Conjugation of Antibodies with Bifunctional Chelating Agents: Isothiocyanate and Bromoacetamide Reagents, Methods of Analysis, and Subsequent Addition of Metal Ions, Analytical Biochemistry, 1984, pp. 68-78, vol. 142.

(56) References Cited

OTHER PUBLICATIONS

Miederer, Matthias et al., Pharmacokinetics, Dosimetry, and Toxicity of the Targetable Atomic Generator, 225Ac-HuM195, in Non-human Primates, Journal of Nuclear Medicine, 2004, pp. 129-137, vol. 45.

Mirzadeh, Saed et al., Radiometal Labeling of Immunoproteins: Covalent Linkage of 2-(4-Isothiocyanatobenzyl) diethylenetriaminepentaacetic Acid Ligands to Immunoglobulin, Bioconjugate Chemistry, 1990, pp. 59-65, vol. 1.

Mitchell, Paul et al., Targeting Primary Human Ph+ B-Cell Precursor Leukemia-Engrafted SCID Mice Using Radiolabeled Anti-CD19 Monoclonal Antibodies, Journal of Nuclear Medicine, 2003, pp. 1105-1112, vol. 44.

Naraki, Toru et al., γ-Carboxyglutamic acid content of hepatocellular carcinoma-associated des-γ-carboxy prothrombin, Biochimica et Biophysica Acta, 2002, pp. 287-298, vol. 1586.

Nikula, Tuomo K. et al., A Rapid, Single Vessel Method for Preparation of Clinical Grade Ligand Conjugated Monoclonal Antibodies, Nuclear Medicine and Biology, 1995, pp. 387-390, vol. 22, No. 3.

Nikula, Tuomo K. et al., Alpha-Emitting Bismuth Cyclohexylbenzyl DTPA Constructs of Recombinant Humanized Anti-CD33 Antibodies: Pharmacokinetics, Bioactivity, Toxicity and Chemistry, Journal of Nuclear Medicine, 1999, pp. 166-176, vol. 40.

Nolte, Alexis et al., Mirror-design of L-oligonucleotide ligands binding to L-arginine, Nature Biotechnology, 1996, pp. 1116-1119, vol. 14.

Owens, Geoffrey C. et al., Identification of two short internal ribosome entry sites selected from libraries of random oligonucleotides, Proceedings of the National Academy of Sciences USA, 2001, pp. 1471-1476, vol. 98, No. 4.

Pearson, William R. and Lipman, David J., "Improved tools for biological sequence comparison", Proceedings of the National Academy of Sciences USA, 1988, pp. 2444-2448, vol. 85.

Plückthun, A., Antibodies from *Escherichia coli*, The Pharmacology of Monoclonal Antibodies, 1994, pp. 269-315, vol. 113, Chapter 11, Springer-Verlag, New York.

Reiss, Bernd et al., A family of binary gene vectors with low inter-transformant variation, Plant Physiology (Life Science Advances), 1994, pp. 143-149, vol. 13.

Roselli, Mario et al., In Vivo Comparison of CHX-DTPA Ligand Isomers in Athymic Mice Bearing Carcinoma Xernografts, Cancer Biotherapy & Radiopharmaceuticals, 1999, pp. 209-220, vol. 14, No. 3.

Ruegg, Curtis L. et al., Improved in Vivo Stability and Tumor Targeting of Bismuth-labeled Antibody, Cancer Research, 1990, pp. 4221-4226, vol. 50.

Seeber, Stefan et al., A Robust High Throughput Platform to Generate Functional Recombinant Monoclonal Antibodies Using Rabbit B Cells from Peripheral Blood, PLoS One, 2014, e86184, 14 pp., vol. 9, Issue 2.

Settler, Matthieu et al., Novel Orbital Shake Bioreactors for Transient Production of CHO Derived IgGs, Biotechnology Progress, 2007, pp. 1340-1346, vol. 23.

Taketa, Kazuhisa et al., Evaluation of Tumor Markers for the Detection of Hepatocellular Carcinoma in Yangon General Hospital, Myanmar, Acta Medica Okayama, 2002, pp. 317-320, vol. 56, No. 6, Article 7.

Tamura, Katsunori et al., Blasticidin S Deaminase Gene (BSD): a New Selection Marker Gene for Transformation of *Arabidopsis thaliana* and Nicotiana tabacum, Bioscience, Biotechnology, and Biochemistry, 1995, pp. 2336-2338, vol. 59, No. 12.

Thompson, Julie D. et al., CLUSTAL W: improving the sensitivity of progressive multiple sequence alignment through sequence weighting, position-specific gap penalties and weight matrix choice, Nucleic Acids Research, 1994, pp. 4673-4680, vol. 22, No. 22.

Toyoda, Hidenori et al., Novel method to measure serum levels of des-gamma-carboxy prothrombin for hepatocellular carcinoma in patients taking warfarin: A preliminary report, Cancer Science, 2012, pp. 921-925, vol. 103.

Uehara, Soichiro et al., Distribution of the heterogeneity of des-γ-carboxyprothrombin in patients with hepatocellular carcinoma, Journal of Gastroenterology and Hepatology, 2005, pp. 1545-1552, vol. 20, No. 10.

Verel, Iris et al., Quantitative 89Zr Immuno-PET for In Vivo Scouting of 90Y-Labeled Monoclonal Antibodies in Xenograft-Bearing Nude Mice, Journal of Nuclear Medicine, 2003, pp. 1663-1670, vol. 44.

Wurm, Florian M., Production of recombinant protein therapeutics in cultivated mammalian cells, Nature Biotechnology, 2004, pp. 1393-1398, vol. 22, No. 11.

Yamaguchi, Isao et al., Development of des-γ-carboxy prothrombin (DCP) measuring reagent using the LiBASys clinical analyzer, Clinical Chemistry and Laboratory Medicine, 2008, pp. 411-416, vol. 46, No. 3.

\* cited by examiner

BINDING AGENT AND ASSAY FOR PIVKA

CROSS-REFERENCE TO RELATED APPLICATIONS

This application is a continuation of International Application No. PCT/EP2018/068871 filed Jul. 12, 2018, which claims priority to European Application No. 17181242.3 filed Jul. 13, 2017, the disclosures of which are hereby incorporated by reference in their entirety.

The present disclosure relates to a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1. Also disclosed are a method for measuring a subset of undercarboxylated PIVKA-II and a method for diagnosing HCC based on such specific binding agent.

BACKGROUND OF THE INVENTION

The protein Prothrombin II, also known as Factor II, undergoes a post-synthetic modification in the presence of Vitamin K wherein ten glutamate (GLA) residues in the GLA domain are carboxylated to γ-carboxy glutamic acid. The carboxylation process is aberrant in the diseased state and incomplete. Due to this incomplete carboxylation not mature prothrombin but rather PIVKA-II (Protein Induced by Vitamin K Absence/Antagonist-II) is formed. PIVKA-II is a large glycoprotein having a 72 KDa molecular mass and known to be elevated in the case of hepatocellular carcinoma (HCC) patients (Liebman et al., The New England Journal of Medicine (1984), 310 (22), pages 1427-1431; Fujiyama et al., Hepatogastroenterology (1986), 33, pages 201-205; Marreo et al., Hepatology (2003), 37, pages 1114-1121).

Liver cancer is the seventh most common cancer and the second cause of death from cancer worldwide. The incidence rate and mortality rate were 10.1 and 9.5 per 100,000 persons in 2012. Hepatocellular carcinoma (HCC) is the major histologic type among primary liver cancers occurring worldwide, accounting for 70% to 85% of the total burden. HCC can be treated by resection, liver transplantation, or local ablation with radiofrequency for patients diagnosed at an early stage.

The marker PIVKA-II is considered to be of major relevance in the early diagnosis of HCC and several immuno assays for measurement of PIVKA-II have been developed. However, due to the fact that ten different carboxylation sites exist and may be carboxylated or not carboxylated and due to stepwise carboxylation of individual glutamic acid residues into γ-carboxy glutamic acid a huge variety of so-called "under-carboxylated" forms of PIVKA-II exists.

Several partially carboxylated prothrombin variants have been shown in patients with a hereditary defect in vitamin K-dependent carboxylation (Goldsmith et al. J. Clin. Invest. 1982; 69, 1253-1260, Borowski et al. J. Biol. Chem. 1985; 260 (16): 9258-64), HCC patients and patients on warfarin therapy (Uehara, et al. Clin. Chim. Acta 1999; 289 (1-2): 33-44). Different carboxylation patterns may correlate with both the functionality of prothrombin and severity of disease, respectively.

The sequence of carboxylation of individual glutamic acid residues into γ-carboxy glutamic acid within the Gla-domain (amino acids 1 to 46 of mature prothrombin) and its significance for prothrombin function was extensively studied.

Uehara et al. (1999) showed that 10 Gla residues of human prothrombin are carboxylated in a certain order, starting with Gla residue 26 followed by Gla residues 25, 16, 29, 20, 19, 14, 32, 7 to 6. Additionally, Gla 16 plays an important role in functionality of prothrombin, loss of the carboxylation at this site leads to the deficiency of coagulant activity and phospholipid binding (Borowski et al. J. Biol. Chem. 1986; 261 (32): 14969-75)

In existing commercially available kits for detection of PIVKA-II mainly the anti-PIVKA-II monoclonal antibody MU-3 is applied (Eidia's and Fujirebio's PIVKA-II assays). The epitope of MU-3 is located between amino acids (AAs) 17-27, with the glutamic acid residues in positions 19 (Glu 19) and 20 (Glu 20) being essential and the glutamic acid residue in position 25 (Glu 25) significantly augmenting the binding of this antibody (Motohara et al. Pediatr. Res. 1985; 19: 354-357, Naraki et al. Biochim. Biophys. Acta 2002; 1586: 287-298).

The IVD Abbott ARCHITECT PIVKA-II assay makes use of the monoclonal antibody coined 3C10. The epitope bound by this antibody has been shown to be essentially equivalent to the MU-3 epitope (Kinukawa et al. Clin. Biochem. 2015; 48 (16-17): 1120-5).

Several commercially available assays for PIVKA-II have been compared. A high correlation (Passing-Bablok correlation coefficient >0.95) between WAKO DCP, Abbott ARCHITECT PIVKA-II, Sanko Junyaku and Eisai Picolumi PIVKA-II and Fujirebio PIVKA-II Lumipulse assay was shown (Kinukawa et al. Clin Biochem. 2015; 48 (16-17): 1120-5, and in the respective package inserts of PIVKA-II Lumipulse, Fujirebio; DCP-Assay, WAKO; Architect PIVKA-II, Abbott). It would thus appear that all these assays detect the same subset (forms) of under-carboxylated PIVKA-II.

Sekisui has developed a sandwich immuno assay based on the two monoclonal antibodies P11 and P16 (WO 2012/002345; Toyoda, H. et al., Cancer Science, 103 (2012) 921-925). One of these monoclonal antibodies binds to the N-terminal amino acids of PIVKA-II while the other one appears to bind somewhere within amino acids 60 to 156 of PIVKA-II. As shown in several papers an assay based on these two monoclonal antibodies appears to bind to another subset of under-carboxylated PIVKA-II forms.

While all commercially available PIVKA-II assays correlate well to each other, the problem and challenge exists whether assays can be developed that detect other subsets of under-carboxylated PIVKA-II than the routinely used assays and if so, whether such assays could lead to clinically meaningful results.

It has now surprisingly been found that novel monoclonal antibodies can be developed and used that exhibit different binding properties as compared to the gold standard monoclonal antibody MU-3. The epitope of these novel monoclonal antibodies requires the presence of Glu 16, while presence of Glu 25 is not required for efficient binding of these novel antibodies. A sandwich immuno assay based on these novel antibodies, despite only intermediate correlation with the commercially available PIVKA-II assays, surprisingly was found to yield clinically meaningful data, especially regarding improved specificity of the assay at the cut-off set for high clinical sensitivity (e.g. at 90%).

SUMMARY OF THE INVENTION

The present invention discloses a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1.

Further disclosed is a method of detecting PIVKA-II in a sample, the method comprising the steps of: a) contacting the sample with a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1; for a time and under conditions sufficient for the formation of a specific binding agent-PIVKA-II complex; and b) detecting the presence of the specific binding agent-PIVKA-II complex, wherein the presence of the specific binding agent-PIVKA-II complex indicates the presence of PIVKA-II in the sample.

Also disclosed is a method of detecting PIVKA-II in a sample comprising the steps of: a) contacting the sample with a first specific binding agent to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1 and a second specific binding agent to PIVKA-II, wherein the second specific binding agent is detectably labeled, for a time and under conditions sufficient to form a first specific binding agent-PIVKA-II-second specific binding agent complex; and b) measuring the complex formed in (a), thereby detecting the PIVKA-II in the sample.

Also disclosed is a method of detecting PIVKA-II in a sample comprising the steps of: a) contacting the sample with a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1; for a time and under conditions sufficient for the formation of a specific binding agent-PIVKA-II complex; b) adding a second specific binding agent to PIVKA-II to the first specific binding agent-PIVKA-II complex, wherein the second specific binding agent binds to an epitope on PIVKA-II that is not part of SEQ ID NO:1 and is detectably labeled, for a time and under conditions sufficient to form first specific binding agent-PIVKA-II-second specific binding agent complex; and c) measuring the complex formed in (b), thereby detecting the presence of PIVKA-II in the sample.

Also disclosed is a method of diagnosing HCC in a patient suspected of having HCC, comprising the steps of: a) obtaining a sample from the patient; b) contacting the sample with a first specific binding agent to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1; and a second specific binding agent to PIVKA-II, wherein the second specific binding agent is detectably labeled, for a time and under conditions sufficient to form a first specific binding agent-PIVKA-II-second specific binding agent complex; c) measuring the complex formed in (b), thereby measuring the amount of PIVKA-II present in the sample, wherein an amount of PIVKA-II greater than a reference level is indicative of the presence of HCC in the patient.

Further disclosed is a method of diagnosing HCC in a patient suspected of having HCC, comprising the steps of: a) obtaining a sample from the patient; b) contacting the sample with a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1; for a time and under conditions sufficient for the formation of a specific binding agent-PIVKA-II complex; c) adding a second specific binding agent to PIVKA-II to the first specific binding agent-PIVKA-II complex, wherein the second specific binding agent binds to an epitope on PIVKA-II that is not part of SEQ ID NO:1 and is detectably labeled, for a time and under conditions sufficient to form a first specific binding agent-PIVKA-II-second specific binding agent complex; d) measuring the complex formed in (c), thereby measuring the amount of PIVKA-II present in the sample, wherein an amount of PIVKA-II greater than a predetermined level is indicative of the presence of HCC in the patient.

Further disclosed are the use of a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1 in the measurement of PIVKA-II as well as a kit for detecting and/or quantifying an amount of PIVKA-II in a sample comprising such specific binding agent.

The formation of the antibody-PIVKA-II-antibody sandwich and its binding streptavidin-coated microparticles is schematically depicted. DCP (descarboxy-prothrombin) is an alternative name for PIVKA-II and "RU" indicates the ruthenium label bound to the second anti-PIVKA-II antibody.

Figure 2:
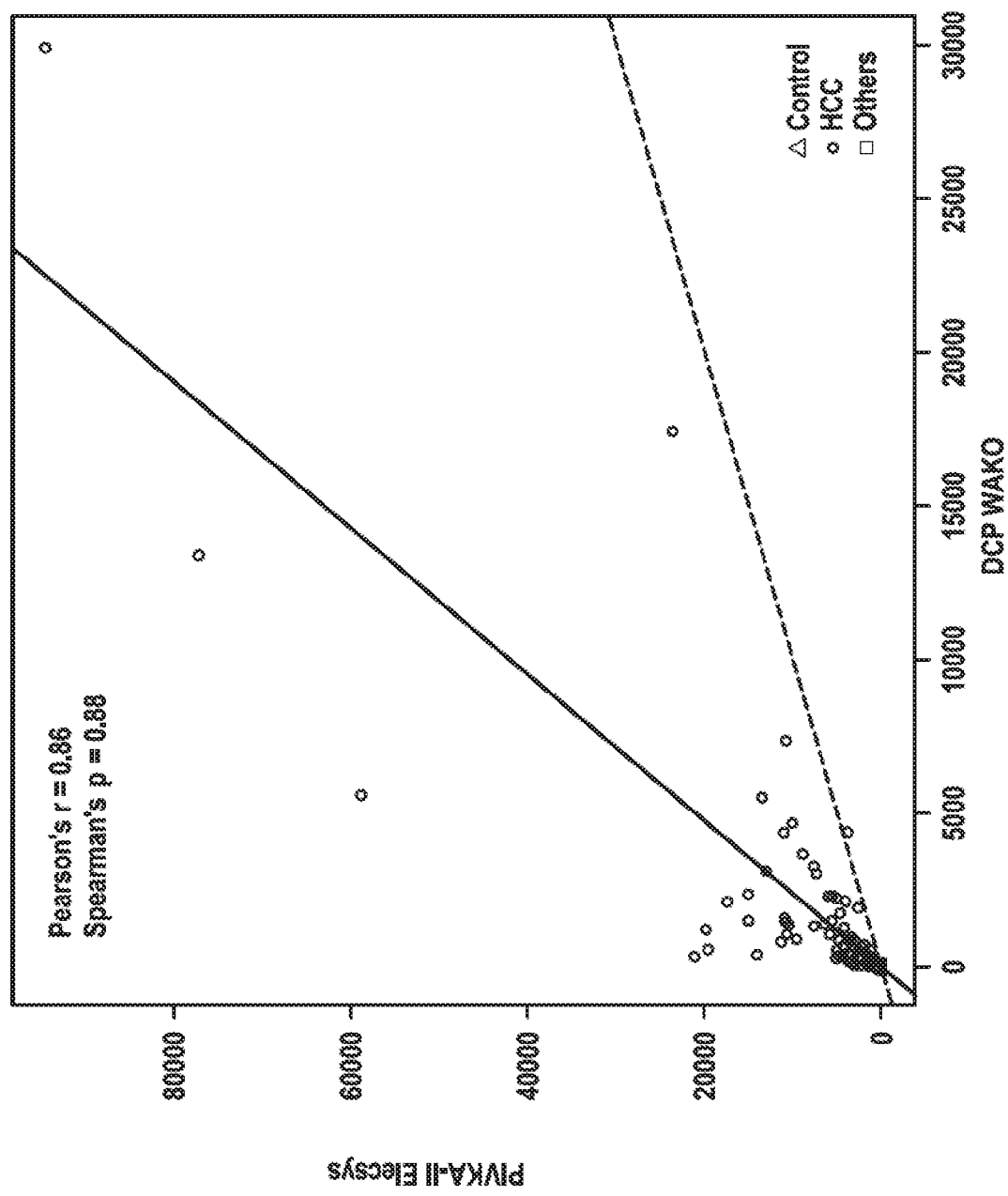

FIG. 2: Method comparison of PIVKA-II Elecsys vs. DCP WAKO Values as measured in the PIVKA-II Elecsys® assay vs. values as measured in the DCP WAKO assay are compared. The three groups consisting of HCC patients, controls and Others (i.e., Cholangiocarcinoma (CCC) or mixed HCC/CCC patients or patients suspected to have HCC/CCC) are shown with different symbols. Deming regression for all points (continuous line), and reference line (dashed line/reference diagonal line with slope as 1 and intercept as 0) is plotted. The correlation coefficients found were Pearson's r=0.86 and Spearman's p=0.88, respectively. Samples from patients treated by Warfarin were excluded.

Figure 3:
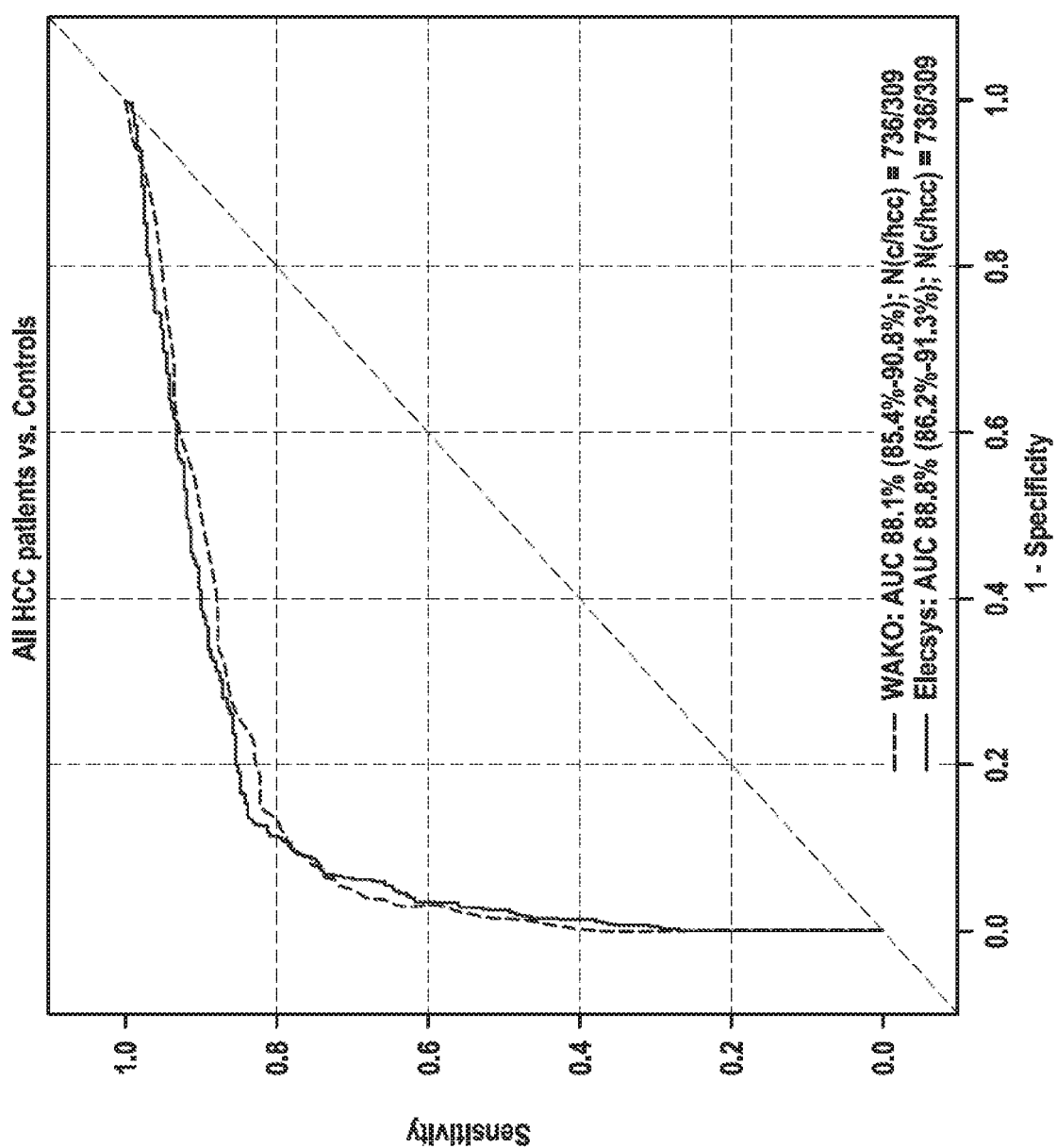

FIG. 3: Clinical performance of WAKO DCP and Elecsys PIVKA-II/all HCC In this Figure the AUCs for the WAKO DCP assay and Elecsys PIVKA-II assay, respectively, for all HCC patients (BCLC stages 0-D) vs controls are shown. For the high sensitivity area the Elecsys PIVKA-II assay shows better specificity than the WAKO DCP test.

Figure 4:
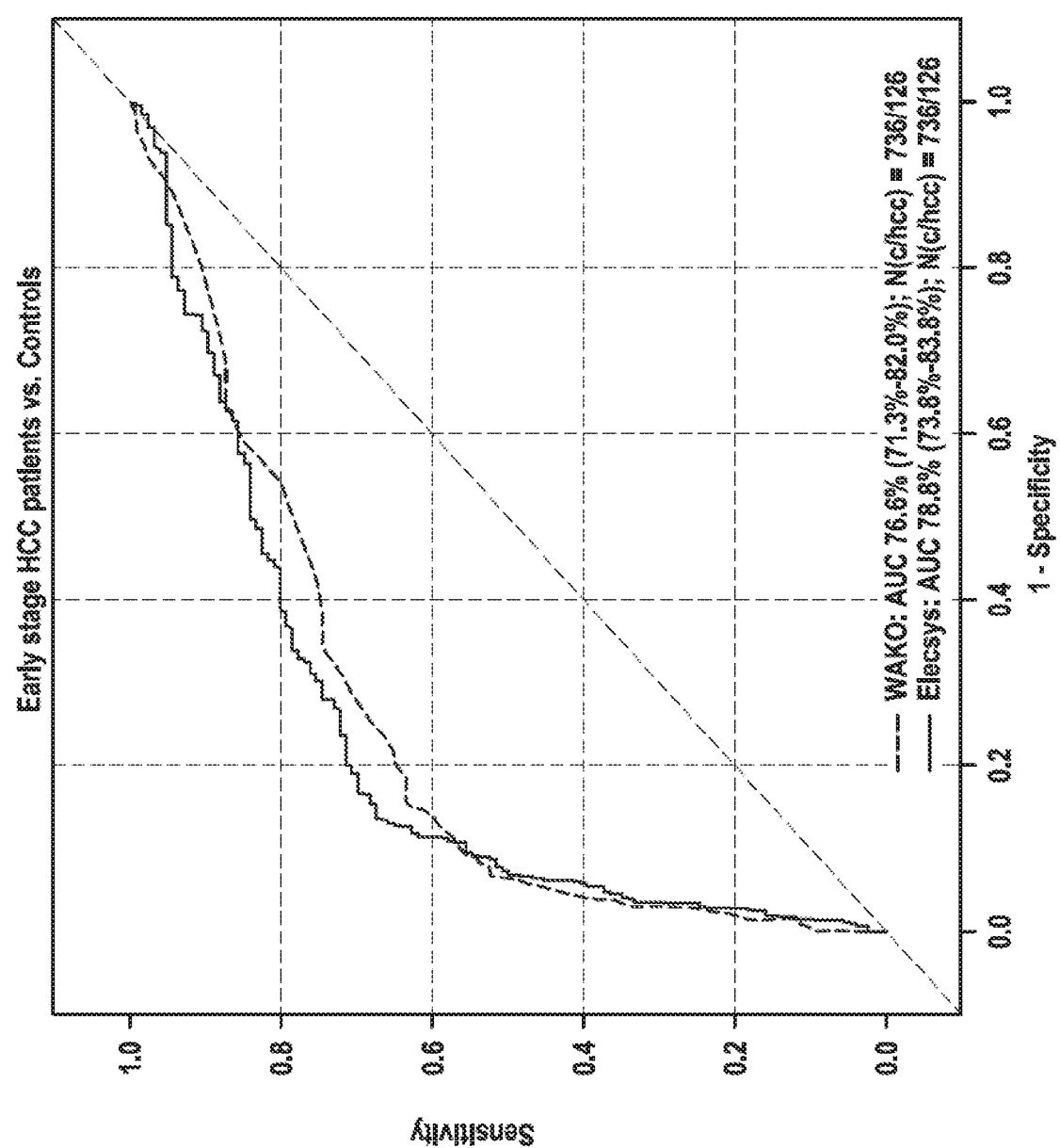

FIG. 4: Clinical performance of WAKO DCP and Elecsys PIVKA-II/early HCC In this Figure the AUCs for the WAKO DCP assay and Elecsys PIVKA-II assay, respectively, for all HCC patients (BCLC stages 0 and A) vs controls are shown. For the high sensitivity areas (60-90%) the Elecsys PIVKA-II assay shows better specificity than the WAKO DCP test.

DETAILED DESCRIPTION OF THE INVENTION

The present disclosure relates to a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1.

As used in this specification and the appended claims, the singular forms "a", "an", and "the" include plural referents, unless the content clearly dictates otherwise.

Preprothrombin (SEQ ID NO:5) is synthesized intracellular and processed to ("mature") prothrombin by cleaving off the first 43 N-terminal amino acids (signal-peptide and pro-peptide sequences→SEQ ID NO:6) and by γ-carboxylation of the glutamic residues at positions 6, 7, 12, 14, 16, 19, 20, 25, 26 and 31 of the prothrombin polypeptide. In the circulation and over time, prothrombin also becomes degraded into a variety of degradation products. Of special interest with respect to detection of under-carboxylation are those prothrombin cleavage (degradation) products that comprise at least the so-called GLA-domain (SEQ ID NO:7). The prothrombin cleavage products of major relevance are the so-called F1/F2-fragment (SEQ ID NO:8) and the so-called F1-fragment (SEQ ID NO:9), respectively.

The peptide sequence of SEQ ID NO:1 correspond to amino acid positions 55 to 70 of preprothrombin (SEQ ID NO:5), i.e. to amino acid positions 12 to 27 of (undercarboxylated and "mature") prothrombin. In the peptide of SEQ ID NO:1 all glutamic acid residues are not γ-carboxylated. Thus, the synthetic peptide of SEQ ID NO:1 corresponds to and mimics PIVKA-II-forms that are not γ-carboxylated at position 19 and are also not γ-carboxylated at positions 20 and 25, respectively.

The peptide sequence of SEQ ID NO:2 also corresponds to amino acid positions 55 to 70 of preprothrombin (SEQ ID NO:5), i.e. to amino acid positions 12 to 27 of (partially carboxylated) prothrombin. The peptide of SEQ ID NO:2 comprises a γ-carboxylated glutamic acid that corresponds to γ-carboxylated glutamic acid at position 19 of mature prothrombin. With other words, this peptide corresponds to and mimics PIVKA-forms that are γ-carboxylated at position 19 (but neither at positions 20 and 25, respectively).

The peptide sequence of SEQ ID NO:3 also corresponds to amino acid positions 55 to 70 of preprothrombin (SEQ ID NO:5), i.e. to amino acid positions 12 to 27 of (partially carboxylated) prothrombin. The peptide of SEQ ID NO:2 comprises a γ-carboxylated glutamic acid that corresponds to γ-carboxylated glutamic acid at position 25 of mature prothrombin. With other words, this peptide corresponds to and mimics PIVKA-II forms that are γ-carboxylated at position 25 (but neither at positions 19 and 20, respectively).

As the skilled artisan will appreciate, the peptide of SEQ ID NO:1 corresponds to amino acid positions 55 to 70 of preprothrombin (SEQ ID NO:5), i.e. to amino acid positions 12 to 27 of non-carboxylated prothrombin. This sequence, as well as the partially gamma-carboxylated sequences (SEQ ID NO:2, 3, or 4) spanning the same stretch of amino acids, comprise two cysteine residues. Under the synthesis conditions chosen according to the present disclosure care has been taken that the two cysteines are oxidized and form a cystine bridge. Thus in all the synthetic peptides comprising SEQ ID NOs: 1, 2, 3 and 4 as well as the sequences of SEQ ID NOs:32, 33 and 34, respectively, used/disclosed herein and/or mentioned in the sequence listing the two cysteine residues are oxidized to from a cystine bridge.

In one embodiment the specific binding agent binding to PIVKA-II is an isolated specific binding agent binding to PIVKA-II. An "isolated" specific binding agent, for example an isolated antibody, is one which has been identified and separated and/or recovered from a component of its natural environment. Contaminant components of its natural environment are materials which would interfere with research, diagnostic or therapeutic uses for the specific bind agent, e.g. an antibody, and may include enzymes, hormones, and other proteinaceous or nonproteinaceous solutes. In some embodiments, a specific binding agent is purified (1) to greater than 90% by weight as determined by, for example, the Lowry method, and in some embodiments, to greater than 95% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain.

Ordinarily, an isolated specific binding agent, e.g. an isolated antibody will be prepared by at least one purification step e.g. using protein purification techniques well known in the art.

The term "specific binding agent" refers to a natural or non-natural molecule that specifically binds to a target. Examples of specific binding agents include, but are not limited to, proteins, peptides and nucleic acids. In certain embodiments, a specific binding agent is an antibody or a nucleic acid.

In certain embodiments, a specific binding agent is an antibody. In certain embodiments, a specific binding agent comprises the antigen binding region of an antibody. The terms target and antigen can be used interchangeably. In one embodiment the target is an antigen and the specific binding agent is an antibody. A specific binding agent has at least an affinity of $10^7$ l/mol for its corresponding target molecule. The specific binding agent in one embodiment has at least an affinity of $10^8$ l/mol or better, or in a further embodiment of at least $10^9$ l/mol or better for its target molecule.

In one embodiment the specific binding agent as disclosed herein is selected from the group consisting of an antibody or an aptamer.

In one embodiment the specific binding agent is a specifically binding nucleic acid also known as aptamer.

The term "aptamer" refers to a nucleic acid that recognizes and binds to polypeptides. Aptamers can be isolated by selection methods such as SELEX (see e.g. Jayasena (1999) Clin. Chem., 45, 1628-50; Klug and Famulok (1994) M. Mol. Biol. Rep., 20, 97-107; U.S. Pat. No. 5,582,981) from a large pool of different single-stranded RNA molecules. Aptamers can also be synthesized and selected in their mirror-image form, for example as the L-ribonucleotide (Nolte et al. (1996) Nat. Biotechnol., 14, 1116-9; Klussmann et al. (1996) Nat. Biotechnol., 14, 1112-5). Forms which have been isolated in the later way enjoy the advantage that they are not degraded by naturally occurring ribonucleases and, therefore, possess greater stability.

In the context of the present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Typically, a peptide has a length of up to 4, 6, 8, 10, 12, 15, 18 or 20 amino acids. A peptide has an amino end and a carboxyl end, unless it is a cyclic peptide.

In the context of the present invention, the term "polypeptide" refers to a single linear chain of amino acids bonded together by peptide bonds and typically comprises at least about 21 amino acids, i.e. at least 21, 22, 23, 24, 25, etc. amino acids. A polypeptide can be one chain of a protein that is composed of more than one chain or it can be the protein itself if the protein is composed of one chain.

The term "synthetic" in the context of peptide is fully clear to the person skilled in the art and merely used to indicate that the peptide has not been isolated from natural sources but has rather been obtained by chemical synthesis in vitro.

The term "binding preference" or "binding preference" indicates that under otherwise comparable conditions one out of two alternative antigens or targets is better bound than the other one. The specific binding agent according to the present disclosure strongly binds to a peptide of SEQ ID NO:1 and less so to a peptide of SEQ ID NO:2. The specific binding to these two peptides, as well as to other peptides, like e.g. SEQ ID NO:3 is assessed as described in example 3. In brief, biotinylated peptides are used comprising the sequences to be analyzed. They are assessed under the assay conditions of example 3 and the signal (counts) obtained for each (biotinylated) peptide analyzed is compared to the signal obtained with the biotinylated peptide comprising SEQ ID NO:1.

The specific binding agent to PIVKA-II as disclosed herein meets at least the two criteria of a) preferential binding of SEQ ID NO:1 over SEQ ID NO:2 by at least 10-fold and of b) binding to the peptide of SEQ ID NO:3 as good or better as to the peptide of SEQ ID NO:1. With other words and different to the MU-3 antibody and similar antibodies known in the art, the specific binding agent of the present invention binds to an epitope that either does not comprise the glutamic acid position 25 of PIVKA-II or that is independent of the presence or absence of a carboxylation of the glutamic acid at position 25 of PIVKA-II.

As the skilled artisan will fully appreciate the experimental assessment of binding strength or binding preference like any other experiment is subject to some variation. Such variation may e.g. lead to plus/minus 20% in signal intensity. Such variation accordingly is within the limits given in absolute numbers, e.g. 50% has to be understood as ranging from 40% to 60%. A comparative binding to one target that is found to be as good as the binding to another target (i.e. 100%) accordingly can be acknowledged if such comparison yields results in the range of 80 to 120% (signal for target one divided by signal for target two and multiplied by 100). In one embodiment the binding properties of a binding agent according to the present invention is assessed as disclosed in example 3. The expression "binding at least as good" means that the specific binding agent binds with equal or greater binding affinity. Along the same lines "an at least 10-fold binding preference" means binding with an at least 10-fold greater binding affinity.

The present disclosure also relates to an isolated specific binding agent binding to PIVKA-II characterized in that it binds to a synthetic peptide of SEQ ID NO:1, has an at least 15-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1.

In one embodiment the present invention relates the present disclosure relates to a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1, that is further characterized in having a binding preference for a peptide of SEQ ID NO: 1 as compared to a peptide of SEQ ID NO:4. With other words in this embodiment the specific binding agent to PIVKA-II binds better to a peptide having a glutamic acid residue in both the positions corresponding to amino acids 19 and 20 of PIVKA-II as compared to a peptide having a glutamic acid in position 19 but a γ-carboxy glutamic acid in position 20. However, the binding preference relating to glutamic acid at position 20 as compared to γ-carboxy glutamic acid at position 20 is by far not as pronounced as with the prior art binding agents, i.e. like the MU-3 antibody.

In one embodiment the specific binding agent according to the present disclosure is an antibody.

In one embodiment the specific binding agent as disclosed herein is a monoclonal antibody.

The overall structure of antibodies is well known in the art and comprises of two heavy chains and two light chains, connected by disulfide bonds. The heavy chains and the light chains each consist of one constant domain and one variable domain. Binding specificity to an antigen is provided by the variable domains of the light and heavy chains that form the antibody. More specifically, the parts of antibodies that determine their specificity and make contact with a specific ligand are referred to as the complementarity determining regions (CDRs). The CDRs are the most variable part of the molecule and contribute to the diversity of these molecules. There are three CDR regions CDR1, CDR2 and CDR3 in each variable domain, embedded into four framework regions (FW). As used herein, CDR-HC (or CDR(HC)) depicts a CDR region of a variable heavy chain and CDR-LC (or CDR(LC)) relates to a CDR region of a variable light chain. Similarly, FW-HC (or FW(HC)) depicts a framework region of a variable heavy chain and FW-LC (or FW(LC)) relates to a framework region of a variable light chain.

The term "comprising", as used in accordance with the present invention, denotes that further sequences/components can be included in addition to the specifically recited sequences and/or components. However, this term also encompasses that the claimed subject-matter consists of exactly the recited sequences and/or components.

In those embodiments where the antibody of the invention includes more than the recited amino acid sequence, additional amino acids extend can be present at either the N-terminal end, or the C-terminal end, or both. Additional sequences can include e.g. sequences introduced e.g. for purification or detection, as discussed in detail herein below. Furthermore, where individual sequences "comprise" the recited sequence, they also can include additional amino acids at either the N-terminal end, or the C-terminal end, or both.

In context of the present invention, the term "antibody" relates to full immunoglobulin molecules as well as to antigen binding fragments thereof, like, Fab, Fab', F(ab')$_2$, Fv. Furthermore, the term relates to modified and/or altered antibody molecules, as well as to recombinantly or synthetically generated/synthesized antibodies. The term "antibody" also comprises bifunctional antibodies, trifunctional antibodies, fully-human antibodies, chimeric antibodies, and antibody constructs, like single chain Fvs (scFv) or antibody-fusion proteins.

A "Fab fragment" as used herein is comprised of one light chain and the $C_H1$ and variable regions of one heavy chain. The heavy chain of a Fab molecule cannot form a disulfide bond with another heavy chain molecule. A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule. A "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

Fab/c fragment contain both Fc and Fab determinants, wherein an "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

The "Fv region" comprises the variable regions from both the heavy and light chains, but lacks the constant regions. "Single-chain Fvs" (also abbreviated as "scFv") are antibody fragments that have, in the context of the present invention, the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen binding. Techniques described for the production of single chain antibodies are described, e.g., in Plückthun in The Pharmacology of Monoclonal Antibodies, Rosenburg and Moore eds. Springer-Verlag, N.Y. 113 (1994), 269-315.

The term "fully-human antibody" as used herein refers to an antibody which comprises human immunoglobulin protein sequences only. Nonetheless, a fully human antibody may contain murine carbohydrate chains if produced in a mouse, in a mouse cell or in a hybridoma derived from a mouse cell or it may contain rat carbohydrate chains if produced in a rat, in a rat cell, or in a hybridoma derived from a rat cell. Similarly, a fully human antibody may contain hamster carbohydrate chains if produced in a hamster, in a hamster cell, such as e.g. CHO cells, or in a hybridoma derived from a hamster cell. On the other hand, a "mouse antibody" or "murine antibody" is an antibody that comprises mouse (murine) immunoglobulin protein sequences only, while a "rat antibody" or a "rabbit antibody" is an antibody that comprises rat or rabbit immunoglobulin sequences, respectively, only. As with fully human antibodies, such murine, rat or rabbit antibodies may contain carbohydrate chains from other species, if produced in such an animal or a cell of such an animal. For example, the antibodies may contain hamster carbohydrate chains if produced in a hamster cell, such as e.g. CHO cells, or in a hybridoma derived from a hamster cell. Fully-human antibodies can be produced, for example, by phage display which is a widely used screening technology which enables production and screening of fully human antibodies. Also phage antibodies can be used in context of this invention. Phage display methods are described, for example, in U.S. Pat. Nos. 5,403,484, 5,969,108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397).

The term "chimeric antibodies" refers to antibodies that comprise a variable region of a human or non-human species fused or chimerized to an antibody region (e.g., constant region) from another species, either human or non-human (e.g., mouse, horse, rabbit, dog, cow, chicken).

As mentioned above, the term "antibody" also encompasses antibody constructs, such as antibody-fusion proteins, wherein the antibody comprises (an) additional domain(s), e.g. for the isolation and/or preparation of recombinantly produced constructs, in addition to the domains defined herein by specific amino acid sequences.

The antibody of the present invention can be produced such that it is a recombinant antibody, for example a recombinant human antibody, a heterologous antibody or a hetero-hybrid antibody. The term "recombinant (human) antibody" includes all (human sequence) antibodies that are prepared, expressed, created or isolated by recombinant means, such as antibodies isolated from an animal (e.g., a mouse) that is transgenic for human immunoglobulin genes, antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism that is not the transgenic non-human animal, and generally from a species other than that of the transgenic non-human animal.

The term "hetero-hybrid antibody" refers to an antibody having light and heavy chains that originate from different organisms. For example, an antibody having a human heavy chain associated with a murine light chain is a hetero-hybrid antibody. Examples of hetero-hybrid antibodies include chimeric and humanized antibodies.

Prior art antibodies against PIVKA-II, like MU-3, for binding to PIVKA-II or corresponding synthetic peptides are strongly dependent on the presence of glutamic acid in position 20 (and partially dependent on the presence of a glutamic acid at position 25). If γ-carboxy glutamic acid is present at position 20 those prior art antibodies hardly show any binding to such peptide and with all likelihood to the corresponding PIVKA-II forms being γ-carboxylated at position 20. However, and quite different, the antibodies as disclosed herein are much less dependent on the presence of glutamic acid in position 20. In one embodiment the present invention relates to a specific binding agent as defined above that is further characterized in a relative binding to SEQ ID NO:4 as compared to SEQ ID NO: 1 in the range of 40 to less than 80% and in a further embodiment in the range of 50 to 80%.

Accordingly, the present invention relates to an antibody that specifically binds to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1 wherein said antibody is further characterized in that the CDRs comprise the following amino acid sequences or a variant thereof that differs in at most one amino acid substitution per CDR:

(i) a CDR1 comprising the amino acid sequence of SEQ ID NO:10, a CDR2 comprising the amino acid sequence of SEQ ID NO:11, and a CDR3 comprising the amino acid sequence of SEQ ID NO:12 in the light chain variable domain, and a CDR1 comprising the amino acid sequence of SEQ ID NO:13, a CDR2 comprising the amino acid sequence of SEQ ID NO:14, and a CDR3 comprising the amino acid sequence of SEQ ID NO:15 in the heavy chain variable domain;

(ii) a CDR1 comprising the amino acid sequence of SEQ ID NO:18, a CDR2 comprising the amino acid sequence of SEQ ID NO:19, and a CDR3 comprising the amino acid sequence of SEQ ID NO:20 in the light chain variable domain, and a CDR1 comprising the amino acid sequence of SEQ ID NO:21, a CDR2 comprising the amino acid sequence of SEQ ID NO:22, and a CDR3 comprising the amino acid sequence of SEQ ID NO:15 in the heavy chain variable domain.

(iii) a CDR1 comprising the amino acid sequence of SEQ ID NO:18, a CDR2 comprising the amino acid sequence of SEQ ID NO:11, and a CDR3 comprising the amino acid sequence of SEQ ID NO:20 in the light chain variable domain, and a CDR1 comprising the amino acid sequence of SEQ ID NO:21, a CDR2 comprising the amino acid sequence of SEQ ID NO:25, and a CDR3 comprising the amino acid sequence of SEQ ID NO:15 in the heavy chain variable domain; or (iv) a CDR1 comprising the amino acid sequence of SEQ ID NO:18, a CDR2 comprising the amino acid sequence of SEQ ID NO:11, and a CDR3 comprising the amino acid sequence of SEQ ID NO:28 in the light chain variable domain, and a CDR1 comprising the amino acid sequence of SEQ ID NO:29, a CDR2 comprising the amino acid sequence of SEQ ID NO:25, and a CDR3 comprising the amino acid sequence of SEQ ID NO:15 in the heavy chain variable domain.

The antibody in accordance with the present invention comprises one of the four recited combinations (i) to (iv) of light chain CRDs and heavy chain CRDs. The surrounding framework sequence of the respective variable domain into which the CDRs are incorporated can be chosen by the skilled person without further ado. For example, the framework sequences described further below or the specific framework sequence employed in the appended examples can be used.

In accordance with the present invention, the CDRs can comprise the specifically recited sequence or can differ therefrom in at most one amino acid substitution per CDR. As such, one amino acid in each of the CDRs can be replaced by a different amino acid. It will be appreciated that also encompassed is that an amino acid substitution is present in some, but not all CDRs of one chain or of one antibody.

The term "substitution", in accordance with the present invention, refers to the replacement of an amino acid with another amino acid. Thus, the total number of amino acids remains the same. The deletion of an amino acid at a certain position or the introduction of one (or more) amino acid(s) at a different position, respectively, is explicitly not encompassed by the term "substitution".

Substitutions, in accordance with the present invention, in one embodiment are conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Such similarities include e.g. a similarity in polarity, charge, solubility, hydrophobicity, hydrophilicity, and/or the amphipathic nature of the residues involved. In one embodiment a conservative amino acid substitution is a substitution of one amino acid for another one as comprised within one of the following groups, (i) nonpolar (hydrophobic) amino acids including alanine, valine, leucine, isoleucine, proline, phenylalanine, tyrosine, tryptophan, and methionine; (ii) polar neutral amino acids including glycine, serine, threonine, cysteine, asparagine, and glutamine; (iii) positively charged (basic) amino acids including arginine, lysine, and histidine; and (iv) negatively charged (acidic) amino acids including aspartic acid and glutamic acid.

In one embodiment the present invention relates to an antibody that specifically binds to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1 wherein said antibody is further characterized in that the CDRs comprise the following amino acid sequences or a variant thereof that differs in at most one amino acid substitution per CDR, with the proviso that CDR3 of the heavy chain variable domain consists of the amino acid sequence of SEQ ID NO:15:

(i) a CDR1 comprising the amino acid sequence of SEQ ID NO:10, a CDR2 comprising the amino acid sequence of SEQ ID NO:11, and a CDR3 comprising the amino acid sequence of SEQ ID NO:12 in the light chain variable domain, and a CDR1 comprising the amino acid sequence of SEQ ID NO:13, a CDR2 comprising the amino acid sequence of SEQ ID NO:14, and a CDR3 comprising the amino acid sequence of SEQ ID NO:15 in the heavy chain variable domain;

(ii) a CDR1 comprising the amino acid sequence of SEQ ID NO:18, a CDR2 comprising the amino acid sequence of SEQ ID NO:19, and a CDR3 comprising the amino acid sequence of SEQ ID NO:20 in the light chain variable domain, and a CDR1 comprising the amino acid sequence of SEQ ID NO:21, a CDR2 comprising the amino acid sequence of SEQ ID NO:22, and a CDR3 comprising the amino acid sequence of SEQ ID NO:15 in the heavy chain variable domain.

(iii) a CDR1 comprising the amino acid sequence of SEQ ID NO:18, a CDR2 comprising the amino acid sequence of SEQ ID NO:11, and a CDR3 comprising the amino acid sequence of SEQ ID NO:20 in the light chain variable domain, and a CDR1 comprising the amino acid sequence of SEQ ID NO:21, a CDR2 comprising the amino acid sequence of SEQ ID NO:25, and a CDR3 comprising the amino acid sequence of SEQ ID NO:15 in the heavy chain variable domain; or (iv) a CDR1 comprising the amino acid sequence of SEQ ID NO:18, a CDR2 comprising the amino acid sequence of SEQ ID NO:11, and a CDR3 comprising the amino acid sequence of SEQ ID NO:28 in the light chain variable domain, and a CDR1 comprising the amino acid sequence of SEQ ID NO:29, a CDR2 comprising the amino acid sequence of SEQ ID NO:25, and a CDR3 comprising the amino acid sequence of SEQ ID NO:15 in the heavy chain variable domain.

In one embodiment, the CDRs comprise the sequences specifically recited above, i.e. without any amino acid variation.

The light chain variable regions/domains/sequences of both heavy and light chains, respectively, comprise the CDRs, determining the specificity of the antibodies, and the more generic frame work regions, "holding the CDRs in place".

A light chain variable domain/sequence consists of framework regions (FWs) and CDRs as represented in formula I:

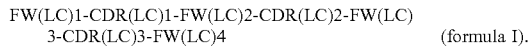

(formula I).

A heavy chain variable domain/sequence consists of FWs and CDRs as represented in formula II:

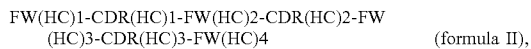

(formula II),

The primary structure shown in formula I represents the order of the components of the light chain variable domain of the antibody of the present invention from the N-terminus to the C-terminus. The primary structure shown in formula II represents the order of the components of the heavy chain variable domain of the antibody of the present invention from the N-terminus to the C-terminus. In each case, framework region (FW) 1 represents the most N-terminal part of the respective variable chain domain, while FW 4 represents the most C-terminal part of the respective variable chain domain.

The skilled artisan can perfectly deduce the sequence of each FW-region once, as in the present disclosure, the full length variable chain sequence and the sequences of the CDRs comprised therein are given.

Furthermore, the present disclosure relates to an antibody that specifically binds to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1, wherein said antibody is further characterized in that it comprises:

(i) a light chain variable sequence of SEQ ID NO:16, comprising a CDR1 of SEQ ID NO:10, a CDR2 of SEQ ID NO:11, and a CDR3 of SEQ ID NO:12 and a heavy chain variable sequence of SEQ ID NO:17, comprising a CDR1 of SEQ ID NO:13, a CDR2 of SEQ ID NO:14, and a CDR3 of SEQ ID NO:15;

(ii) a light chain variable sequence of SEQ ID NO:23, comprising a CDR1 of SEQ ID NO:18, a CDR2 of SEQ ID NO:19, and a CDR3 of SEQ ID NO:20 and a heavy chain variable sequence of SEQ ID NO:24, comprising a CDR1 of SEQ ID NO:21, a CDR2 of SEQ ID NO:22, and a CDR3 of SEQ ID NO:15;

(iii) a light chain variable sequence of SEQ ID NO:26, comprising a CDR1 of SEQ ID NO:18, a CDR2 of SEQ ID NO:11, and a CDR3 of SEQ ID NO:20 and a heavy chain variable sequence of SEQ ID NO:27, comprising a CDR1 of SEQ ID NO:21, a CDR2 of SEQ ID NO:25, and a CDR3 of SEQ ID NO:15; or (iv) a light chain variable sequence of SEQ ID NO:30, comprising a CDR1 of SEQ ID NO:18, a CDR2 of SEQ ID NO:11, and a CDR3 of SEQ ID NO:28 and a heavy chain variable sequence of SEQ ID NO:31, comprising a CDR1 of SEQ ID NO:29, a CDR2 of SEQ ID NO:25, and a CDR3 of SEQ ID NO:15;

wherein each of the FWs is as contained in the above given variable chain sequences or is a variant thereof that is at least 85% identical to the FW-sequence as disclosed via the variable chain sequences above and wherein each of the CDRs is as given above or differs in at most one amino acid substitution:

With regard to the CDRs and variants thereof, the above provided definitions and specifically exemplified embodiments apply mutatis mutandis.

With regard to the framework regions, a certain degree of variability is also envisaged herein, i.e. the individual FWs can comprise the, or consist of the specifically recited amino acid sequence or of an amino acid sequence at least 85% identical thereto. In one further embodiment, the identity is at least 90%. In yet a further embodiment the identity is at least 95%.

In accordance with the present invention, the term "% sequence identity" describes the number of matches ("hits") of identical amino acids of two or more aligned amino acid sequences as compared to the number of amino acid residues making up the overall length of the amino acid sequences (or the overall compared part thereof). Percent identity is determined by dividing the number of identical residues by the total number of residues and multiplying the product by 100. In other terms, using an alignment, the percentage of amino acid residues that are the same (e.g., 85% identity) may be determined for two or more sequences or sub-sequences when these (sub)sequences are compared and aligned for maximum correspondence over a window of comparison, or over a designated region as measured using a sequence comparison algorithm as known in the art, or when manually aligned and visually inspected.

Those having skill in the art know how to determine percent sequence identity between/among sequences using, for example, algorithms such as those based on the NCBI BLAST algorithm (Altschul, S. F. et al. [1997] Nucleic Acids Res. 25:3389-3402), CLUSTALW computer program (Tompson, J. D. et al. [1994] Nucleic Acids Res. 22:4673-4680) or FASTA (Pearson, W. R. & Lipman, D. J. [1988] Proc. Natl. Acad. Sci. U.S.A. 85:2444-2448). In one embodiment, the NCBI BLAST algorithm is employed in accordance with this invention. For amino acid sequences, the BLASTP program uses as default a word length (W) of 3, and an expectation (E) of 10. The BLOSUM62 scoring matrix (Henikoff, S. & Henikoff, J. G. [1992] Proc. Natl. Acad. Sci. U.S.A. 89:10915-10919) uses alignments (B) of 50, expectation (E) of 10, M=5, N=4, and a comparison of both strands. Accordingly, in those embodiments where a % sequence identity is indicated, all the amino acid sequences having a sequence identity of at least 85% as determined with the NCBI BLAST program fall under the scope of said embodiments.

The above described degree of variation in the framework regions as compared to the respective specifically recited amino acid sequence can be due to the substitution, insertion, addition, or deletion of (an) amino acid(s).

The term "substitution", has been defined herein above. In those cases where more than one amino acid is to be substituted, each amino acid is independently replaced with another amino acid, i.e. for each amino acid that is removed a different amino acid is introduced at the same position.

The term "insertion", in accordance with the present invention, refers to the addition of one or more amino acids to the specifically recited amino acid sequence, wherein the addition is not to the N- or C-terminal end of the polypeptide.

The term "addition", in accordance with the present invention, refers to the addition of one or more amino acids to the specifically recited amino acid sequence, either to the N- or C-terminal end of the polypeptide, or to both.

The term "deletion", as used in accordance with the present invention, refers to the loss of one or more amino acids from the specifically recited amino acid sequence.

In one embodiment, the variation in the amino acid sequences of the framework regions is due to the substitution of (an) amino acid(s). Substitutions, as defined herein above, can be conservative amino acid substitutions or non-conservative amino acid substitutions. The definitions and specifically exemplified embodiments provided above with regard to the term "substitution" apply mutatis mutandis. In one embodiment, the substitutions in the framework regions are conservative amino acid substitutions.

In a further embodiment of the antibody of the invention, the antibody comprises a light chain variable domain consisting of framework regions (FWs) and CDRs as represented in formula I above, and a heavy chain variable domain consisting of FWs and CDRs as represented in formula II above, wherein the FWs comprise the amino acid sequences disclosed via the variable chain sequences or a variant thereof that is at least 85% identical thereto and wherein the CDRs comprise the following amino acid sequences:

(i) a light chain variable sequence of SEQ ID NO:16, comprising a CDR1 of SEQ ID NO:10, a CDR2 of SEQ ID NO:11, and a CDR3 of SEQ ID NO:12 and a heavy chain variable sequence of SEQ ID NO:17, comprising a CDR1 of SEQ ID NO:13, a CDR2 of SEQ ID NO:14, and a CDR3 of SEQ ID NO:15;

(ii) a light chain variable sequence of SEQ ID NO:23, comprising a CDR1 of SEQ ID NO:18, a CDR2 of SEQ ID NO:19, and a CDR3 of SEQ ID NO:20 and a heavy chain variable sequence of SEQ ID NO:24, comprising a CDR1 of SEQ ID NO:21, a CDR2 of SEQ ID NO:22, and a CDR3 of SEQ ID NO:15;

(iii) a light chain variable sequence of SEQ ID NO:26, comprising a CDR1 of SEQ ID NO:18, a CDR2 of SEQ ID NO:11, and a CDR3 of SEQ ID NO:20 and a heavy chain variable sequence of SEQ ID NO:27, comprising a CDR1 of SEQ ID NO:21, a CDR2 of SEQ ID NO:25, and a CDR3 of SEQ ID NO:15; or (iv) a light chain variable sequence of SEQ ID NO:30, comprising a CDR1 of SEQ ID NO:18, a CDR2 of SEQ ID NO:11, and a CDR3 of SEQ ID NO:28 and a heavy chain variable sequence of SEQ ID NO:31, comprising a CDR1 of SEQ ID NO:29, a CDR2 of SEQ ID NO:25, and a CDR3 of SEQ ID NO:15.

Because the parts of formula I and formula II defined herein as FWs are amino acid sequences that form part of the frame or scaffold of the variable chain regions, substitution within said sequences, in particular in form of conservative amino acid substitutions, will in many cases not affect the binding capability of the anti-PIVKA-II antibody.

The present invention further relates to an antibody that specifically binds to PIVKA-II is characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1, said antibody comprising (i) a light chain variable domain consisting of an amino acid sequence that is at least 85% identical to the light chain variable domain consisting of the amino acid sequence of SEQ ID NO:16, and a heavy chain variable domain consisting of an amino acid sequence that is at least 85% identical to the heavy chain variable domain consisting of the amino acid sequence of SEQ ID NO:17;

(ii) a light chain variable domain consisting of an amino acid sequence that is at least 85% identical to the light chain variable domain consisting of the amino acid sequence of SEQ ID NO:23, and a heavy chain variable domain consisting of an amino acid sequence that is at least 85% identical to the heavy chain variable domain consisting of the amino acid sequence of SEQ ID NO:24;

(iii) a light chain variable domain consisting of an amino acid sequence that is at least 85% identical to the light chain variable domain consisting of the amino acid sequence of SEQ ID NO:26, and a heavy chain variable domain consisting of an amino acid sequence that is at least 85% identical to the heavy chain variable domain consisting of the amino acid sequence of SEQ ID NO:27; or (iv) a light chain variable domain consisting of an amino acid sequence that is at least 85% identical to the light chain variable domain consisting of the amino acid sequence of SEQ ID NO:30, and a heavy chain variable domain consisting of an amino acid sequence that is at least 85% identical to the heavy chain variable domain consisting of the amino acid sequence of SEQ ID NO:31.

All definitions and specifically exemplified embodiments provided herein above with regard to the anti-PIVKA-II antibody of the invention, in particular the cited degrees and types of variations apply mutatis mutandis.

In one embodiment, the antibody that specifically binds to PIVKA-II, is characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1:

(i) comprises as light chain variable domain the amino acid sequence of SEQ ID NO:16 and as heavy chain variable domain the amino acid sequence of SEQ ID NO:17 (i.e. corresponding to the variable chain regions of monoclonal the antibody designated as 7A10 in the appended examples);

(ii) comprises as light chain variable domain the amino acid sequence of SEQ ID NO:23 and as heavy chain variable domain the amino acid sequence of SEQ ID NO:24 (i.e. corresponding to the variable chain regions of monoclonal the antibody designated as 4E8 in the appended examples);

(iii) comprises as light chain variable domain the amino acid sequence of SEQ ID NO:26 and as heavy chain variable domain the amino acid sequence of SEQ ID NO:27 (i.e. corresponding to the variable chain regions of monoclonal the antibody designated as 9A6 in the appended examples); or (iv) comprises as light chain variable domain the amino acid sequence of SEQ ID NO:30 and as heavy chain variable domain the amino acid sequence of SEQ ID NO:31 (i.e.

corresponding to the variable chain regions designated as 13H7 in the appended examples).

The above recited sequences for the variable light and heavy chain regions are the amino acid sequences that have been employed in the appended examples. Full-length amino acid sequences for the light and heavy chains present in the antibodies employed in the examples (that comprise said variable domains) are represented in SEQ ID NOs: 16, 23, 26 and 30 and SEQ ID NOs:17, 24, 27 and 31, respectively. As is shown in the examples, these anti-PIVKA-II antibodies provide for an excellent binding efficiency and specificity.

The present invention further relates to a nucleic acid molecule encoding a light chain variable region of any one of the antibodies of the invention defined herein above. This nucleic acid molecule is referred to herein as the first nucleic acid molecule of the invention. Furthermore, the present invention also relates to a nucleic acid molecule encoding a heavy chain variable region of any one of the antibodies of the invention defined herein above. This nucleic acid molecule is referred to herein as the second nucleic acid molecule of the invention.

In accordance with the present invention, the term "nucleic acid molecule", also referred to as nucleic acid sequence or polynucleotide herein, includes DNA, such as cDNA or genomic DNA.

The nucleic acid molecules of the invention can e.g. be synthesized by standard chemical synthesis methods and/or recombinant methods, or produced semi-synthetically, e.g. by combining chemical synthesis and recombinant methods. Ligation of the coding sequences to transcriptional regulatory elements and/or to other amino acid encoding sequences can be carried out using established methods, such as restriction digests, ligations and molecular cloning.

In accordance with the present invention, the first nucleic acid molecule of the invention encodes a light chain variable region of an antibody that specifically binds to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1:

(i) comprising a CDR1 comprising the amino acid sequence of SEQ ID NO:10 or a variant thereof that differs in at most one amino acid substitution, a CDR2 comprising the amino acid sequence of SEQ ID NO:11 or a variant thereof that differs in at most one amino acid substitution, and a CDR3 comprising the amino acid sequence of SEQ ID NO:12 or a variant thereof that differs in at most one amino acid substitution;

(ii) comprising a CDR1 comprising the amino acid sequence of SEQ ID NO:18 or a variant thereof that differs in at most one amino acid substitution, a CDR2 comprising the amino acid sequence of SEQ ID NO:19 or a variant thereof that differs in at most one amino acid substitution, and a CDR3 comprising the amino acid sequence of SEQ ID NO:20 or a variant thereof that differs in at most one amino acid substitution;

(iii) comprising a CDR1 comprising the amino acid sequence of SEQ ID NO:18 or a variant thereof that differs in at most one amino acid substitution, a CDR2 comprising the amino acid sequence of SEQ ID NO:11 or a variant thereof that differs in at most one amino acid substitution, and a CDR3 comprising the amino acid sequence of SEQ ID NO:20 or a variant thereof that differs in at most one amino acid substitution;

(iv) comprising a CDR1 comprising the amino acid sequence of SEQ ID NO:18 or a variant thereof that differs in at most one amino acid substitution, a CDR2 comprising the amino acid sequence of SEQ ID NO:11 or a variant thereof that differs in at most one amino acid substitution, and a CDR3 comprising the amino acid sequence of SEQ ID NO:28 or a variant thereof that differs in at most one amino acid substitution;

(v) an amino acid sequence that is at least 85% identical to the light chain variable domain consisting of the amino acid sequence of SEQ ID NO:16;

(vi) an amino acid sequence that is at least 85% identical to the light chain variable domain consisting of the amino acid sequence of SEQ ID NO:23;

(vii) an amino acid sequence that is at least 85% identical to the light chain variable domain consisting of the amino acid sequence of SEQ ID NO:26; or (viii) an amino acid sequence that is at least 85% identical to the light chain variable domain consisting of the amino acid sequence of SEQ ID NO:30.

Similarly, the second nucleic acid molecule of the invention encodes a heavy chain variable region of an antibody that specifically binds to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1:

(i) comprising a CDR1 comprising the amino acid sequence of SEQ ID NO:13 or a variant thereof that differs in at most one amino acid substitution, a CDR2 comprising the amino acid sequence of SEQ ID NO:14 or a variant thereof that differs in at most one amino acid substitution, and a CDR3 comprising the amino acid sequence of SEQ ID NO:15 or a variant thereof that differs in at most one amino acid substitution;

(ii) comprising a CDR1 comprising the amino acid sequence of SEQ ID NO:21 or a variant thereof that differs in at most one amino acid substitution, a CDR2 comprising the amino acid sequence of SEQ ID NO:22 or a variant thereof that differs in at most one amino acid substitution, and a CDR3 comprising the amino acid sequence of SEQ ID NO:15 or a variant thereof that differs in at most one amino acid substitution;

(iii) comprising a CDR1 comprising the amino acid sequence of SEQ ID NO:21 or a variant thereof that differs in at most one amino acid substitution, a CDR2 comprising the amino acid sequence of SEQ ID NO:25 or a variant thereof that differs in at most one amino acid substitution, and a CDR3 comprising the amino acid sequence of SEQ ID NO:15 or a variant thereof that differs in at most one amino acid substitution;

(iv) comprising a CDR1 comprising the amino acid sequence of SEQ ID NO:29 or a variant thereof that differs in at most one amino acid substitution, a CDR2 comprising the amino acid sequence of SEQ ID NO:25 or a variant thereof that differs in at most one amino acid substitution, and a CDR3 comprising the amino acid sequence of SEQ ID NO:15 or a variant thereof that differs in at most one amino acid substitution;

(v) an amino acid sequence that is at least 85% identical to the heavy chain variable domain consisting of the amino acid sequence of SEQ ID NO:17;

(vi) an amino acid sequence that is at least 85% identical to the heavy chain variable domain consisting of the amino acid sequence of SEQ ID NO:24;

(vii) an amino acid sequence that is at least 85% identical to the heavy chain variable domain consisting of the amino acid sequence of SEQ ID NO:27; or (viii) an amino acid sequence that is at least 85% identical to the heavy chain variable domain consisting of the amino acid sequence of SEQ ID NO:31.

The present invention further relates to a vector comprising the first nucleic acid molecule of the invention, i.e. a nucleic acid molecule encoding a light chain variable region of any one of the antibodies of the invention defined herein above. The present invention further relates to a vector comprising the second nucleic acid molecule of the invention, i.e. a nucleic acid molecule encoding a heavy chain variable region of any one of the antibodies of the invention defined herein above. Such vectors are also referred to herein as the "individual vector(s) of the invention".

Many suitable vectors are known to those skilled in molecular biology, the choice of which depends on the desired function. Non-limiting examples of vectors include plasmids, cosmids, viruses, bacteriophages and other vectors used conventionally in e.g. genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994).

In one embodiment, the vector is an expression vector. An expression vector according to this invention is capable of directing the replication and the expression of the nucleic acid molecule of the invention in a host and, accordingly, provides for the expression of the variable chain domains of the anti-PIVKA-II antibodies of the present invention encoded thereby in the selected host. In a further embodiment, the vector(s) comprise(s) further sequences to ensure that not only said variable chain domains of the invention are expressed, but also the full-length IgG antibodies comprising said variable chain domains of the invention.

Expression vectors can for instance be cloning vectors, binary vectors or integrating vectors. Expression comprises transcription of the nucleic acid molecule, for example into a translatable mRNA. In one embodiment, the vector is a eukaryotic expression plasmid for the transient recombinant expression of the heavy chain and/or the light chain of monoclonal rabbit antibodies. Such vectors have been specifically developed for antibody expression but also antibody production by e.g. transient transfection of eukaryotic cells e.g. HEK 293 or derivatives thereof or CHO cells.

Non-limiting examples of vectors include pQE-12, the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1, pTRE, pCAL-n-EK, pESP-1, pOP13CAT, the E-027 pCAG Kosak-Cherry (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Non-limiting examples for plasmid vectors suitable for *Pichia pastoris* comprise e.g. the plasmids pAO815, pPIC9K and pPIC3.5K (all Invitrogen). Another vector suitable for expressing proteins in *Xenopus* embryos, zebrafish embryos as well as a wide variety of mammalian and avian cells is the multipurpose expression vector pCS2+.

Generally, vectors can contain one or more origins of replication (ori) and inheritance systems for cloning or expression, one or more markers for selection in the host, e.g., antibiotic resistance, and one or more expression cassettes. In addition, the coding sequences comprised in the vector can be ligated to transcriptional regulatory elements and/or to other amino acid encoding sequences using established methods. Such regulatory sequences are well known to those skilled in the art and include, without being limiting, regulatory sequences ensuring the initiation of transcription, internal ribosomal entry sites (IRES) (Owens, G. C. et al. [2001] Proc. Natl. Acad. Sci. U.S.A. 98:1471-1476) and optionally regulatory elements ensuring termination of transcription and stabilization of the transcript. Non-limiting examples for such regulatory elements ensuring the initiation of transcription comprise promoters, a translation initiation codon, enhancers, insulators and/or regulatory elements ensuring transcription termination, which are to be included downstream of the nucleic acid molecules of the invention. Further examples include Kozak sequences and intervening sequences flanked by donor and acceptor sites for RNA splicing, nucleotide sequences encoding secretion signals or, depending on the expression system used, signal sequences capable of directing the expressed protein to a cellular compartment or to the culture medium. The vectors may also contain an additional expressible polynucleotide coding for one or more chaperones to facilitate correct protein folding.

Additional examples of suitable origins of replication include, for example, the full length ColE1, a truncated ColEI, the SV40 viral and the M13 origins of replication, while additional examples of suitable promoters include, without being limiting, the cytomegalovirus (CMV) promoter, SV40-promoter, RSV-promoter (Rous sarcome virus), the lacZ promoter, the tetracycline promoter/operator (tet$^{p/o}$), chicken β-actin promoter, CAG-promoter (a combination of chicken β-actin promoter and cytomegalovirus immediate-early enhancer), the gai10 promoter, human elongation factor 1α-promoter, AOX1 promoter, GAL1 promoter CaM-kinase promoter, the lac, trp or tac promoter, the T7 or T5 promoter, the lacUV5 promoter, the *Autographa californica* multiple nuclear polyhedrosis virus (AcMNPV) polyhedral promoter or a globin intron in mammalian and other animal cells. One example of an enhancer is e.g. the SV40-enhancer. Non-limiting additional examples for regulatory elements ensuring transcription termination include the SV40-poly-A site, the tk-poly-A site, the rho-independent lpp terminator or the AcMNPV polyhedral polyadenylation signals. Further non-limiting examples of selectable markers include dhfr, which confers resistance to methotrexate (Reiss, Plant Physiol. (Life Sci. Adv.) 13 (1994), 143-149), npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to blasticidin S (Tamura, Biosci. Biotechnol. Biochem. 59 (1995), 2336-2338).

In a further embodiment, the vector is a eukaryotic expression plasmid containing an expression cassette consisting of a 5' CMV promoter including Intron A, and a 3' BGH polyadenylation sequence. In addition to the expression cassette, the plasmid can contain a pUC18-derived origin of replication and a beta-lactamase gene conferring ampicillin resistance for plasmid amplification in *E. coli*. For secretion of the antibodies, a eukaryotic leader sequence can be cloned 5' of the antibody gene.

Suitable bacterial expression hosts comprise e. g. strains derived from JM83, W3110, KS272, TG1, K12, BL21 (such as BL21(DE3), BL21(DE3)PlysS, BL21(DE3)RIL, BL21 (DE3)PRARE) or Rosettaâ. For vector modification, PCR amplification and ligation techniques, see Sambrook & Russel [2001] (Cold Spring Harbor Laboratory, NY).

The nucleic acid molecules and/or vectors of the invention can be designed for introduction into cells by e.g. chemical based methods (polyethylenimine, calcium phosphate, liposomes, DEAE-dextrane, nucleofection), non chemical methods (electroporation, sonoporation, optical transfection, gene electrotransfer, hydrodynamic delivery or naturally occurring transformation upon contacting cells with the nucleic acid molecule of the invention), particle-based methods (gene gun, magnetofection, impalefection) phage vector-based methods and viral methods. For example, expression vectors derived from viruses such as retroviruses, vaccinia virus, adeno-associated virus, herpes viruses, Semliki Forest Virus or bovine papilloma virus, may be used for delivery of the nucleic acid molecules into targeted cell population. Additionally, baculoviral systems can also be used as vector in eukaryotic expression system for the nucleic acid molecules of the invention. In one embodiment, the nucleic acid molecules and/or vectors of the invention are designed for transformation of chemical competent *E. coli* by calcium phosphate and/or for transient transfection of HEK293 and CHO by polyethylenimine- or lipofectamine-transfection.

The present invention further relates to a vector comprising a nucleic acid molecule encoding a light chain variable domain according to option (i) to (viii) as defined herein above and a matching (e.g. vi) and vi) above) heavy chain variable domain according to option (i) to (viii) defined herein above;

In one embodiment, the vector is an expression vector.

All definitions and specifically exemplified embodiments provided herein above with regard to the vector of the invention, in particular vector types or the regulatory sequences apply mutatis mutandis. This second type of vector relates to a vector comprising at least two nucleic acid molecules, namely one encoding a light chain variable domain and one encoding a heavy chain variable domain. As is evident from the above combinations, the light chain variable domain and heavy chain variable domain are combined in the vector such that the expression of a functional anti-PIVKA-II antibody of the invention is enabled. This second type of vector is also referred to herein as the "combination vector of the invention".

The present invention further relates to a host cell or non-human host comprising:

(i) the combination vector of the invention; or (ii) the individual vector of the invention comprising the first nucleic acid molecule of the invention, i.e. a nucleic acid molecule encoding a light chain variable region in accordance with the invention and the individual vector of the invention comprising the second nucleic acid molecule of the invention, i.e. a nucleic acid molecule encoding a heavy chain variable region of the invention, wherein these two vectors comprise the nucleic acid molecules encoding for matching light chain and heavy chain variable regions as defined above.

The host cell can be any prokaryotic or eukaryotic cell. The term "prokaryote" is meant to include all bacteria which can be transformed, transduced or transfected with DNA or DNA or RNA molecules for the expression of a protein of the invention. Prokaryotic hosts may include gram negative as well as gram positive bacteria such as, for example, *E. coli, S. typhimurium, Serratia marcescens, Corynebacterium (glutamicum), Pseudomonas (fluorescens), Lactobacillus, Streptomyces, Salmonella* and *Bacillus subtilis*.

The term "eukaryotic" is meant to include yeast, higher plant, insect and mammalian cells. Typical mammalian host cells include, Hela, HEK293, H9, Per.C6 and Jurkat cells, mouse NIH3T3, NS/0, SP2/0 and C127 cells, COS cells, e.g. COS 1 or COS 7, CV1, quail QC1-3 cells, mouse L cells, mouse sarcoma cells, Bowes melanoma cells and Chinese hamster ovary (CHO) cells. Exemplary mammalian host cells in accordance with the present invention are CHO cells. Other suitable eukaryotic host cells include, without being limiting, chicken cells, such as e.g. DT40 cells, or yeasts such as *Saccharomyces cerevisiae, Pichia pastoris, Schizosaccharomyces pombe* and *Kluyveromyces lactis*. Insect cells suitable for expression are e.g. *Drosophila* S2, *Drosophila* Kc, *Spodoptera* Sf9 and Sf21 or *Trichoplusia* Hi5 cells. Suitable zebrafish cell lines include, without being limiting, ZFL, SJD or ZF4.

The described vector(s) can either integrate into the genome of the host or can be maintained extrachromosomally. Once the vector has been incorporated into the appropriate host, the host is maintained under conditions suitable for high level expression of the nucleic acid molecules, and as desired, the collection and purification of the antibody of the invention may follow. Appropriate culture media and conditions for the above described host cells are known in the art.

In one embodiment, the recited host is a mammalian cell, such as a human cell or human cell line. In a further embodiment, the host cell transformed with the vector(s) of the invention is HEK293 or CHO. In yet a further embodiment, the host cell transformed with the vector(s) of the invention is CHO. These host cells as well as suitable media and cell culture conditions have been described in the art, see e.g. Baldi L. et al., Biotechnol Prog. 2005 January-February; 21(1):148-53, Girard P. et al., Cytotechnology 2002 January; 38(1-3):15-21 and Stettler M. et al., Biotechnol. Prog. 2007 November-December; 23(6):1340-6.

With regard to the term "vector comprising" in accordance with the present invention it is understood that further nucleic acid sequences are present in the vectors that are necessary and/or sufficient for the host cell to produce an anti-PIVKA-II antibody of the invention. Such further nucleic acid sequences are e.g. nucleic acid sequences encoding the remainder of the light chain as well as nucleic acid sequences encoding the remainder of the heavy chain.

The host cell or non-human host, in accordance with the present invention, comprises either one vector encoding both the light chain and heavy chain variable regions as defined herein above or it comprises two separate vectors, wherein one vector carries a nucleic acid molecule encoding a light chain variable region in accordance with the present invention and the second vector carries a nucleic acid molecule encoding a matching heavy chain variable region in accordance with the present invention. Thus, where the first vector carries a nucleic acid molecule encoding a light chain variable region in accordance with option (i) herein above, then the second vector carries a nucleic acid molecule encoding a heavy chain variable region also in accordance with option (i) above. The same applies mutatis mutandis to options (ii) to (viii).

Accordingly, in each case, expression of those nucleic acid molecules is linked to each other that are required to be present within one antibody molecule to ensure the production of an anti-PIVKA-II antibody of the invention consisting of the binding capabilities described herein above.

The host cells in accordance with this embodiment may e.g. be employed to produce large amounts of the anti-PIVKA-II antibodies of the present invention. Said host cells are produced by introducing the above described vector(s) into the host. The presence of said vector(s) in the host then mediates the expression of the nucleic acid molecules encoding the above described light chain variable domains and heavy chain variable domains of the anti-PIVKA-II antibodies of the invention. As described herein above, the vector(s) of the invention can comprise further sequences enabling the expression of full length IgG antibodies, thereby resulting in the production of full length IgG antibodies by the host cells, wherein said antibodies are characterized by the presence of the variable light and/or heavy chain domains in accordance with the present invention.

The present invention further relates to a method for the production of an antibody that specifically binds to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1, the method comprising culturing the host cell of the invention under suitable conditions and isolating the antibody produced.

In accordance with this embodiment, the vector(s) present in the host of the invention is/are either (an) expression vector(s), or the vector(s) mediate(s) the stable integration of the nucleic acid molecule(s) of present invention into the genome of the host cell in such a manner that expression thereof is ensured. Means and methods for selection of a host cell in which the nucleic acid molecules encoding the respective light and heavy chain domains of the anti-PIVKA-II antibody of the present invention have been successfully introduced such that expression of the antibody is ensured are well known in the art and have been described (Browne, S. M. & Al-Rubeai, M. [2007] Trends Biotechnol. 25:425-432; Matasci, M et al. [2008] Drug Discov. Today: Technol. 5:e37-e42; Wurm, F. M. [2004] Nat. Biotechnol. 22:1393-1398).

Suitable conditions for culturing prokaryotic or eukaryotic host cells are well known to the person skilled in the art. For example, bacteria such as e.g. *E. coli* can be cultured under aeration in Luria Bertani (LB) medium, typically at a temperature from 4 to about 37° C. To increase the yield and the solubility of the expression product, the medium can be buffered or supplemented with suitable additives known to enhance or facilitate both. In those cases where inducible promoters control the nucleic acid molecules of the invention in the vector(s) present in the host cell, expression of the polypeptide can be induced by addition of an appropriate inducing agent, such as e.g. anhydrotetracycline. Suitable expression protocols and strategies have been described in the art (e.g. in Dyson, M. R., et al. (2004). BMC Biotechnol. 4, 32-49 and in Baldi, L. et al. (2007) Biotechnol. Lett. 29, 677-684) and can be adapted to the needs of the specific host cells and the requirements of the protein to be expressed, if required.

Depending on the cell type and its specific requirements, mammalian cell culture can e.g. be carried out in RPMI, Williams' E or DMEM medium containing 10% (v/v) FCS, 2 mM L-glutamine and 100 U/ml penicillin/streptomycin. The cells can be kept e.g. at 37° C. or at 41° C. for DT40 chicken cells, in a 5% $CO_2$, water-saturated atmosphere.

A suitable medium for insect cell culture is e.g. TNM+ 10% FCS, SF900 or HyClone SFX-Insect medium. Insect cells are usually grown at 27° C. as adhesion or suspension cultures.

Suitable expression protocols for eukaryotic or vertebrate cells are well known to the skilled person and can be retrieved e.g. from Sambrook, J & Russel, D. W. [2001] (Cold Spring Harbor Laboratory, NY).

In one embodiment, the method is carried out using mammalian cells, such as e.g. CHO or HEK293 cells. In a further embodiment, the method is carried out using CHO cells.

Depending upon the host employed in a recombinant production procedure, the antibody expressed may be glycosylated or may be non-glycosylated. In one embodiment, a plasmid or a virus is used containing the coding sequence of the antibody of the invention and genetically fused thereto an N-terminal FLAG-tag and/or C-terminal His-tag. In a further embodiment, the length of said FLAG-tag is about 4 to 8 amino acids, such as e.g. exactly 8 amino acids. An above described vector can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, loc cit.).

The transformed hosts can be grown in bioreactors and cultured according to techniques known in the art to achieve optimal cell growth. The antibody of the invention can then be isolated from the growth medium. The isolation and purification of the, e.g., microbially expressed antibodies of the invention may be by any conventional means such as, e.g., affinity chromatography (for example using a fusion-tag such as the Strep-tag II or the $His_6$ tag), gel filtration (size exclusion chromatography), anion exchange chromatography, cation exchange chromatography, hydrophobic interaction chromatography, high pressure liquid chromatography (HPLC), reversed phase HPLC or immunoprecipitation. These methods are well known in the art and have been generally described, e.g. in Sambrook, J & Russel, D. W. [2001] (Cold Spring Harbor Laboratory, NY).

It will be appreciated that in accordance with the present invention, the term "isolating the antibody produced" refers to the isolation of the anti-PIVKA-II antibody of the present invention.

Furthermore, the present invention relates to an antibody that specifically binds to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1, wherein the antibody is obtainable or obtained by the method of the invention.

The present invention further relates to a composition comprising at least one of:
(i) the antibody of the invention,
(ii) the nucleic acid molecule of the invention,
(iii) the vector of the invention,
(iv) the host cell of the invention, and/or
(v) the antibody produced by the method of the invention.

The term "composition", as used in accordance with the present invention, relates to a composition which comprises at least one of the recited compounds. It may, optionally, comprise further molecules capable of altering the characteristics of the compounds of the invention thereby, for example, stabilizing, modulating and/or enhancing their function. The composition may be in solid or liquid form and may be, inter alia, in the form of (a) powder(s), (a) tablet(s) or (a) solution(s).

The components of the composition can be packaged in a container or a plurality of containers, for example, sealed ampoules or vials, as an aqueous solution or as a lyophilized formulation for reconstitution. As an example of a lyophilized formulation, 10-ml vials are filled with 5 ml of 1% (w/v) or 10% (w/v) aqueous solution, and the resulting mixture is lyophilized. A solution for use is prepared by reconstituting the lyophilized compound(s) using either e.g. water-for-injection for therapeutic uses or another desired solvent, e.g. a buffer, for diagnostic purposes. Preservatives and other additives may also be present such as, for example, antimicrobials, anti-oxidants, chelating agents, and inert gases and the like.

The various components of the composition may be packaged as a kit with instructions for use.

In one embodiment the present disclosure relates to a method of detecting PIVKA-II in a sample, the method comprising the steps of: a) contacting the sample with a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1; for a time and under conditions sufficient for the formation of a specific binding agent-PIVKA-II complex; and b) detecting the presence of the specific binding agent-PIVKA-II complex, wherein the presence of the specific binding agent-PIVKA-II complex indicates the presence of PIVKA-II in the sample.

In one embodiment the present invention relates to a method of detecting PIVKA-II in a sample comprising the steps of: a) contacting the sample with a first specific binding agent to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1 and a second specific binding agent to PIVKA-II, wherein the second specific binding agent is detectably labeled, for a time and under conditions sufficient to form a first specific binding agent-PIVKA-II-second specific binding agent complex; and b) measuring the complex formed in (a), thereby detecting the PIVKA-II in the sample.

As obvious to the skilled artisan the sample can be contacted with the first and the second specific binding agent in any desired order, i.e. first→second; second→first, or simultaneously, for a time and under conditions sufficient to form a first specific binding agent-PIVKA-II-second specific binding agent complex.

In one embodiment the present disclosure relates to a method of detecting PIVKA-II in a sample comprising the steps of: a) contacting the sample with a first specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1; for a time and under conditions sufficient for the formation of a first specific binding agent-PIVKA-II complex; b) adding a second specific binding agent to PIVKA-II to the first specific binding agent-PIVKA-II complex, wherein the second specific binding agent is detectably labeled, for a time and under conditions sufficient to form a first specific binding agent-PIVKA-II-second specific binding agent complex; and c) measuring the complex formed in (b), thereby detecting the PIVKA-II in the sample.

As the skilled artisan will readily appreciate it is nothing but routine experimentation to establish the time and conditions that are appropriate or that are sufficient for the formation of a complex either between the specific binding agent (to PIVKA-II) and the (PIVKA-II) antigen/analyte (=specific binding agent-antigen/analyte complex) or the formation of the secondary or sandwich complex comprising the first specific bind agent (to PIVKA-II), the (PIVKA-II) antigen/analyte and the second specific bind agent (to PIVKA-II) (=first specific binding agent-antigen/analyte-second specific binding agent complex).

In further embodiments of a method for detecting the analyte PIVKA-II the specific binding agent to PIVKA-II, or at least one of the binding agents used is as defined above.

The detection of the specific binding agent-PIVKA-II complex can be performed by any appropriate means. The person skilled in the art is absolutely familiar with such means/methods.

The term "sample" or "sample of interest" or "test sample" are used interchangeably herein. The sample is an in vitro sample, it will be analysed in vitro and not transferred back into the body. Examples of samples include but are not limited to fluid samples such as blood, serum, plasma, synovial fluid, urine, saliva, and lymphatic fluid, or solid samples such as tissue extracts, cartilage, bone, synovium, and connective tissue. In one embodiment the sample is selected from blood, serum, plasma, synovial fluid and urine. In one embodiment the sample is selected from blood, serum and plasma. In one embodiment the sample is serum or plasma.

The term "reference sample" as used herein, refers to a sample which is analysed in a substantially identical manner as the sample of interest and whose information is compared to that of the sample of interest. A reference sample thereby provides a standard allowing for the evaluation of the information obtained from the sample of interest. A reference sample may be derived from a healthy or normal tissue, organ or individual, thereby providing a standard of a healthy status of a tissue, organ or individual. Differences between the status of the normal reference sample and the status of the sample of interest may be indicative of the risk of disease development or the presence or further progression of such disease or disorder. A reference sample may be derived from an abnormal or diseased tissue, organ or individual thereby providing a standard of a diseased status of a tissue, organ or individual. Differences between the status of the abnormal reference sample and the status of the sample of interest may be indicative of a lowered risk of disease development or the absence or bettering of such disease or disorder The terms "elevated" or "increased" level of an indicator refer to the level of such indicator in the sample being higher in comparison to the level of such indicator in a reference or reference sample. E.g. a protein that is detectable in higher amounts in a fluid sample of one individual suffering from a given disease than in the same fluid sample of individuals not suffering from said disease, has an elevated level.

In certain embodiments a sandwich will be formed comprising the first specific bind agent (to PIVKA-II), the (PIVKA-II) antigen and the second specific binding agent (to PIVKA-II), wherein the second specific binding agent is detectably labeled.

Numerous labels (also referred to as dyes) are available which can be generally grouped into the following categories, all of them together and each of them representing embodiments according the present disclosure:

(a) Fluorescent dyes

Fluorescent dyes are e.g. described by Briggs et al "Synthesis of Functionalized Fluorescent Dyes and Their Coupling to Amines and Amino Acids," J. Chem. Soc., Perkin-Trans. 1 (1997) 1051-1058).

Fluorescent labels or fluorophores include rare earth chelates (europium chelates), fluorescein type labels including FITC, 5-carboxyfluorescein, 6-carboxy fluorescein; rhodamine type labels including TAMRA; dansyl; Lissamine; cyanines; phycoerythrins; Texas Red; and analogs thereof. The fluorescent labels can be conjugated to an aldehyde group comprised in target molecule using the techniques disclosed herein. Fluorescent dyes and fluorescent label reagents include those which are commercially available from Invitrogen/Molecular Probes (Eugene, Oreg., USA) and Pierce Biotechnology, Inc. (Rockford, Ill.).

(b) Luminescent dyes

Luminescent dyes or labels can be further subcategorized into chemiluminescent and electrochemiluminescent dyes.

The different classes of chemiluminogenic labels include luminol, acridinium compounds, coelenterazine and analogues, dioxetanes, systems based on peroxyoxalic acid and their derivatives. For immunodiagnostic procedures predominantly acridinium based labels are used (a detailed overview is given in Dodeigne C. et al., Talanta 51 (2000) 415-439).

The labels of major relevance used as electrochemiluminescent labels are the Ruthenium- and the Iridium-based electrochemiluminescent complexes, respectively. Electrochemiluminescense (ECL) proved to be very useful in analytical applications as a highly sensitive and selective method. It combines analytical advantages of chemiluminescent analysis (absence of background optical signal) with ease of reaction control by applying electrode potential. In general Ruthenium complexes, especially [Ru(Bpy)3]2+ (which releases a photon at ~620 nm) regenerating with TPA (Tripropylamine) in liquid phase or liquid-solid interface are used as ECL-labels. Recently also Iridium-based ECL-labels have been described (WO2012107419(A1)).

(c) Radioactive labels make use of radioisotopes (radionuclides), such as 3H, 11C, 14C, 18F, 32P, 35S, 64Cu, 68Gn, 86Y, 89Zr, 99TC, 111In, 123I, 124I, 125I, 131I, 133Xe, 177Lu, 211At, or 131Bi.

(d) Metal-chelate complexes suitable as labels for imaging and therapeutic purposes are well-known in the art (US 2010/0111856; U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al, J. Immunol. Methods 65 (1983) 147-157; Meares et al, Anal. Biochem. 142 (1984) 68-78; Mirzadeh et al, Bioconjugate Chem. 1 (1990) 59-65; Meares et al, J. Cancer (1990), Suppl. 10:21-26; Izard et al, Bioconjugate Chem. 3 (1992) 346-350; Nikula et al, Nucl. Med. Biol. 22 (1995) 387-90; Camera et al, Nucl. Med. Biol. 20 (1993) 955-62; Kukis et al, J. Nucl. Med. 39 (1998) 2105-2110; Verel et al., J. Nucl. Med. 44 (2003) 1663-1670; Camera et al, J. Nucl. Med. 21 (1994) 640-646; Ruegg et al, Cancer Res. 50 (1990) 4221-4226; Verel et al, J. Nucl. Med. 44 (2003) 1663-1670; Lee et al, Cancer Res. 61 (2001) 4474-4482; Mitchell, et al, J. Nucl. Med. 44 (2003) 1105-1112; Kobayashi et al Bioconjugate Chem. 10 (1999) 103-111; Miederer et al, J. Nucl. Med. 45 (2004) 129-137; DeNardo et al, Clinical Cancer Research 4 (1998) 2483-90; Blend et al, Cancer Biotherapy & Radiopharmaceuticals 18 (2003) 355-363; Nikula et al J. Nucl. Med. 40 (1999) 166-76; Kobayashi et al., J. Nucl. Med. 39 (1998) 829-36; Mardirossian et al, Nucl. Med. Biol. 20 (1993) 65-74; Roselli et al, Cancer Biotherapy & Radiopharmaceuticals, 14 (1999) 209-20).

In one embodiment the second specific binding agent to PIVKA-II used for formation of a sandwich comprising a first specific binding agent, PIVKA-II and the second specific binding agent complex is a polyclonal or a monoclonal antibody.

In one embodiment a sandwich immuno assay method is practiced using a first specific binding agent to PIVKA-II according to the present invention as one partner in such sandwich assay and a second specific binding agent binding to the F1/F2-fragment of PIVKA-II (SEQ ID NO:8) as another binding partner.

In one embodiment the sandwich immuno assay method is practiced using a first specific binding agent to PIVKA-II according to the present invention as one partner in such sandwich assay and a second specific binding agent binding to the F1-fragment of PIVKA-II (SEQ ID NO:9) as another binding partner.

In one embodiment the sandwich immuno assay method is practiced using a first specific binding agent to PIVKA-II according to the present invention as one partner in such sandwich assay and a second specific binding agent binding to the Gla-domain of PIVKA-II (SEQ ID NO:7) as another binding partner.

In the formation of a sandwich comprising, a first specific binding agent, PIVKA-II, and the second specific binding agent; the two specific binding agents are binding to non-overlapping epitopes. In one embodiment the second specific binding agent to PIVKA-II binds to an epitope on PIVKA-II that is not part of SEQ ID NO:1. In one embodiment both, the first and the second specific binding agent, each are an antibody, in one embodiment both of them are a monoclonal antibody.

In one embodiment the present disclosure relates to a method of diagnosing HCC in a patient suspected of having HCC, comprising the steps of: a) obtaining a sample from the patient; b) contacting the sample with a first specific binding agent to PIVKA-II according to any of claims 1 to 5 and a second specific binding agent to PIVKA-II, wherein the second specific binding agent is detectably labeled, for a time and under conditions sufficient to form a first specific binding agent-PIVKA-II-second specific binding agent complex; c) measuring the complex formed in (b), thereby measuring the amount of PIVKA-II present in the sample, wherein an amount of PIVKA-II greater than a reference level is indicative of the presence of HCC in the patient.

In one embodiment the present disclosure relates to a method of diagnosing HCC in a patient suspected of having HCC, comprising the steps of: a) obtaining a sample from the patient; b) contacting the sample with a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1; for a time and under conditions sufficient for the formation of a specific binding agent-PIVKA-II complex; c) adding a second specific binding agent to PIVKA-II to the first specific binding agent-PIVKA-II complex, wherein the second specific binding agent binds to an epitope on PIVKA-II that is not part of SEQ ID NO:1 and is detectably labeled, for a time and under conditions sufficient to form a first specific binding agent-PIVKA-II-second specific binding agent complex; d) measuring the complex formed in (c), thereby measuring the amount of PIVKA-II present in the sample, wherein an amount of PIVKA-II greater than a predetermined level is indicative of the presence of HCC in the patient.

In one embodiment the present disclosure relates to the use of a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1; in the measurement of PIVKA-II.

In one embodiment the present disclosure relates to a kit for detecting and/or quantifying the amount of PIVKA-II in a sample comprising a container containing a specific binding agent binding to PIVKA-II characterized in that it binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1.

The following examples are provided to aid the understanding of the present invention, the true scope of which is set forth in the appended claims. It is understood that modifications can be made in the procedures set forth without departing from the spirit of the invention.

Example 1

Synthesis of Peptide Immunogens for Use in Generation of Monoclonal Anti-PIVKA-II Antibodies
1.1 General Synthesis Method for Peptides Used in Immunogens and in Screening Reagents Peptides were synthesized by means of fluorenylmethyl-oxycarbonyl (Fmoc) solid phase peptide synthesis on a multiple peptide synthesizer e.g. from Protein Technologies, Inc. In this synthesis 4 equivalents of each amino acid derivative were used in each step of the synthesis. Amino acid derivatives were dissolved in dimethylformamide containing 1 equivalent of 1-Hydroxy-7-azabenzotriazol. Peptides were synthesized on Tentagel® resin (Rapp Polymere GmbH, Tübingen). Coupling reactions were carried out for 5 minutes in dimethylformamide as a reaction medium with 4 equivalents HATU (1-[Bis(dimethylamino)methylene]-1H-1,2,3-triazolo[4,5-b]pyridinium 3-oxide hexafluorophosphate) and 8 equivalents of N,N-Diisopropylethylamine relative to resin loading. The Fmoc-group was cleaved off within 8 minutes after each synthesis step using 20% piperidine in dimethyl formamide. Release of the peptide from the synthesis resin and the cleavage of the acid-labile protecting groups was achieved within 3 hours at room temperature with a cocktail containing trifluoroacetic acid, triisopropylsilane, and water (38:1:1). The reaction solution was subsequently mixed with cooled diisopropyl ether to precipitate the peptide. The precipitate was filtered, washed again with cold diisopropyl ether, dissolved in a small amount of aqueous acetic acid and lyophilized. The crude material obtained was purified by preparative RP-HPLC using a gradient of acetonitrile/water containing 0.1% trifluoroacetic acid. The identity of the purified material was checked by means of ion spray mass spectrometry.

1.2 Peptide immunogen 51-73

The peptide ßAla-Ahx-ßAla-ßAla-VRRGN-LERECVEETCSYEEAFEA-NH2 (SEQ ID NO:32) was synthesized, comprising the amino acids 51 to 73 of preprothrombin (SEQ ID NO:5) but for a substitution of the lysine in position 53 by arginine as well as N-terminally an extension by ßAla-Ahx-ßAla-ßAla.

ESI-MS$_{calc}$: M+=3045.4 Da;
ESI-MS$_{exp}$: [M+3H]$^{3+}$=1015.6 Da

Disulfide oxidation of this peptide was the performed as follows. CLEAR-OX™ resin (130 mg, 26 mol) was swollen in dichloromethane (DCM) for 30 min and then washed successively with dimethylformamide (DMF), methanol and acetonitrile. Reduced peptide (16 mg, 8.5 µmol) was dissolved in a mixture of degased ammonium acetate buffer (0.1 M; pH 7.8) and acetonitrile (1:1, 2.5 mL) added to the resin and gently agitated for 4 h. The resin was washed with 50% aqueous acetonitrile and the filtrate lyophilized.

ESI-MS$_{calc}$: M+=3043.4 Da; ESI-MS$_{exp}$: [M+3H]$^{3+}$=1015.2 Da

The next step was the N-terminal conjugation of diethyl squarate (squarate=3-ethoxy-3-cyclobutene-1,2-dione). To a solution of peptide (9 mg, 3 µmol) in ethanol and water (1:1) 3,4-diethoxy-3-cyclobutene-1,2-dione (1.2 eq) was added. The solution was kept at pH 8.0 by addition of sodium carbonate, stirred overnight and subsequently evaporated to dryness.

ESI-MS$_{calc}$: M+=3167.2 Da; ESI-MS$_{exp}$: [M+3H]$^{3+}$=1056.5 Da

Then the peptide-KLH conjugate was synthesized. To a solution of KLH (35 mg) in borate buffer (10 mL, 0.1 M, pH 9.0) squaramide containing peptide (9 mg, 3 µmol) was added. The reaction was incubated overnight at room temperature and dialyzed against phosphate buffer (0.1 M, pH 7.0) to yield 35.3 mg peptide-KLH conjugate.

1.3 Peptide Immunogen 55-70

The peptide ßAla-Ahx-ßAla-ßAla-NLERECVEETCSY-EEA-NH2 (SEQ ID NO:33) was synthesized, comprising the amino acids 55 to 70 of preprothrombin (SEQ ID NO:5) as well as N-terminally an extension by ßAla-Ahx-ßAla-ßAla.

ESI-MS$_{calc}$: M+=2229.0 Da;
ESI-MS$_{exp}$: [M+2H]$^{2+}$=1115.5 Da

Disulfide oxidation of this peptide was the performed as follows. CLEAR-OX™ resin (230 mg, 46 mol) was swollen in DCM for 30 min and then washed successively with DMF, methanol and acetonitrile. Reduced peptide (34 mg, 15.3 µmol) was dissolved in a mixture of degased ammonium acetate buffer (0.1 M; pH 7.8) and acetonitrile (1:1, 5 mL) added to the resin and gently agitated for 4 h. The resin was washed with 50% aqueous acetonitrile and the filtrate lyophilized.

ESI-MS$_{calc}$: M+=2227.0 Da;
ESI-MS$_{exp}$: [M+2H]$^{2+}$=1114.5 Da

The next step was the N-terminal conjugation of diethyl squarate. To a solution of peptide (34 mg, 15.3 µmol) in ethanol and water (1:1) 3,4-diethoxy-3-cyclobutene-1,2-dione (1.5 eq) was added. The solution was kept at pH 8.0 by addition of sodium carbonate, stirred overnight and subsequently evaporated to dryness.

ESI-MS$_{calc}$: M+=2351.4 Da;
ESI-MS$_{exp}$: [M+2H]$^{2+}$=1176.6 Da

Then the peptide-KLH conjugate was synthesized. To a solution of KLH (50 mg) in borate buffer (15 mL, 0.1 M, pH 9.0) squaramide-containing peptide (27.2 mg, 12.2 µmol) was added. The reaction was incubated overnight at room temperature and dialyzed against phosphate buffer (0.1 M, pH 7.0) to yield 49.5 mg peptide-KLH conjugate.

Example 2

Generation of Monoclonal Anti-PIVKA-II Antibodies
2.1 Immunization of Rabbits for Generation of Antibodies Against PIVKA-II Here we describe the development antibodies with the ability to bind to different epitopes within the N-terminal region of PIVKA-II. For the generation of such antibodies, 12-16-weeks old NZW rabbits were immunized with various peptides spanning the N-terminal region of PIVKA-II. To enhance the immunogenicity of the peptides they were coupled to KLH as a carrier protein, as described in Example 1. For immunization peptides covering the AAs 51-73 and 55-70, respectively of preprothrombin were selected. All rabbits were subjected to repeated immunizations. In the first month the animals were immunized weekly. From the second month onwards the animals were immunized once per month. For the first immunization 500 µg KLH-coupled peptide was dissolved in 1 mL 140 mM NaCl and was emulsified in 1 ml complete Freund's Adjuvant (CFA). For all following immunizations, CFA was replaced by Incomplete Freund's Adjuvant (IFA). The titers of the animals were evaluated on day 45 and day 105, respectively, after start of the immunization.

2.2 Titer Analysis

To determine the titers of the immunized animals, serum titrations were performed using a C-terminally biotinylated peptide of SEQ ID NO:1 (=NLERECVEETCSYEEA-E (Biotin-PEG)-NH2 with C/C as disulfide). The peptide was synthesized by means of fluorenylmethyloxycarbonyl (Fmoc) solid phase peptide synthesis on a multiple peptide synthesizer e.g. from Protein Technologies, Inc. For this 4 equivalents of each amino acid derivative were used. Amino acid derivatives were dissolved in dimethylformamide containing 1 equivalent of 1-Hydroxy-7-azabenzotriazol. Peptides were synthesized on Tentagel R resin. Coupling reactions were carried out for 5 minutes in dimethylformamide as a reaction medium with 4 equivalents HATU and 8 equivalents of N,N-Diisopropylethylamine relative to resin loading. The Fmoc-group was cleaved in 8 minutes after each synthesis step using 20% piperidine in dimethyl formamide. Release of the peptide from the synthesis resin and the cleavage of the acid-labile protecting groups was achieved in 3 hours at room temperature with a cocktail containing trifluoroacetic acid, triisopropylsilane, and water (38:1:1). The reaction solution was subsequently mixed with cooled diisopropyl ether to precipitate the peptide. The precipitate was filtered, washed again with cold diisopropyl ether, dissolved in a small amount of aqueous acetic acid and lyophilized. The crude material obtained was purified by preparative RP-HPLC using a gradient of acetonitrile/water containing 0.1% trifluoroacetic acid. The identity of the purified material was checked by means of ion spray mass spectrometry.

Sequence: NLERECVEETCSYEEA-E(Biotin-PEG)-NH2

Abbreviations: DMF=dimethylformamide; DCM=dichloromethane; E(Biotin-PEG)=Nδ-(N-biotinyl-3-(2-(2-(3-aminopropyloxy)-ethoxy)-ethoxypropyl)-L-glutamine; —NH2=C-terminal carboxamide;

ESI-MS$_{calc}$: M+=2459.7 Da; ESI-MS$_{exp}$: [M+2H]$^{2+}$=1231.0 Da

Disulfide Oxidation

CLEAR-OX™ resin (80 mg, 16 mol) was swollen in DCM for 30 min and then washed successively with DMF, methanol and acetonitrile. Reduced peptide (10.4 mg, 4.2 mol) was dissolved in a mixture of degased ammonium acetate buffer (0.1 M; pH 7.8) and acetonitrile (1:1, 1.5 mL) added to the resin and gently agitated for 2 h. The resin was washed with water and the filtrate lyophilized.

ESI-MS$_{calc}$: M+=2457.7 Da; ESI-MS$_{exp}$: [M+2H]$^{2+}$=1230.1 Da

The above biotinylated screening peptide was immobilized on the surface of 96 well streptavidin-coated microtitre plates. For immobilization the biotinylated peptide (100 µl) was incubated in the wells of the microtitre plate for 30 min at a concentration of 100 ng/ml. A small amount of serum of each rabbit (2-3 ml per animal) was collected on day 45 and day 105, respectively, after the start of the immunization campaign. The sera from each rabbit were diluted in PBS with 1% BSA and the dilutions were added to the plates. The sera were tested at dilutions of 1:300, 1:900, 1:2700, 1:8100, 1:24300, 1:72900, 1:218700 and 1:656100, respectively. For the ELISA test 100 µl of the sera at various dilutions were added to the wells of a 96 well plate, which were coated with the respective peptides as described above. The sere were incubated for 30 min at room temperature. Bound antibody was detected with a HRP-labeled F(ab')2 goat anti-rabbit Fcγ (Dianova) and ABTS (Roche) as a substrate. The titer of the analyzed animals was set at 50% signal decrease of the dilution curve.

TABLE 1

Titers after immunization with PIVKA-II peptide immunogens

| immunogen | animal | titer day 45 | titer day 105 |
|---|---|---|---|
| 51-73 | #5913 | 1090 | 1445 |
| 51-73 | #5914 | 280 | 1674 |
| 51-73 | #5915 | 1409 | 4370 |
| 55-70 | #5910 | 1265 | 1707 |
| 55-70 | #5911 | 11418 | 31433 |
| 55-70 | #5912 | 9702 | 13594 |

As can be seen from Table 1, the polyclonal sera from the immunized animals bind to the screening peptide. Therefore all animals were suitable for subsequent antibody development.

2.3 Development of Antibodies Binding to PIVKA-II

In the development of antibodies binding to PIVKA-II, B-cell cloning as described in Seeber et al. (2014), PLoS One. 2014 Feb. 4; 9(2) was used. For the enrichment of antigen reactive B-cells the respective biotinylated screening peptides with sequences homologous to the immunogens were immobilized on streptavidin coated magnetic beads (Miltenyi). For the coating of the beads the peptides were used at a concentration of 250 ng/ml. Afterwards, the peripheral blood mononuclear cell (PBMC) pool of the immunized animals was prepared and incubated with the peptide-coated beads for 1 h. For the enrichment of antigen-reactive B-cells MACS columns (Miltenyi) were used.

B-cell sorting and incubation was done as described in Seeber et al. (2014), PLoS One. 2014 Feb. 4; 9(2). For the so-called Hit-ELISA the respective screening peptides were immobilized on the surface of streptavidin-coated 96 well plates (Greiner Bio-One). The biotinylated peptides were immobilized on plate surfaces at a concentration of 100 ng/ml. Therefore 100 µl of the peptide solution was incubated on the plates for 30 min at room temperature. After washing the plates were blocked with 100 µl 5% BSA for 30 min at room temperature to reduce background signals. The plates were washed again and 30 µl of the rabbit B-cell cultures were transferred to the 96 well plates and incubated for 1 h at room temperature. For the detection of antibodies bound to the screening peptides, HRP-labeled F(ab')2 goat anti-rabbit Fcγ (Dianova) and ABTS (Roche) as a substrate were added. Clones binding their respective screening peptide were selected for subsequent molecular cloning as described in Seeber et al. (2014), PLoS One. 2014 Feb. 4; 9(2).

2.4 Screening of Selected Clones

Human prothrombin was obtained from Haemochrom Diagnostica (Essen, Germany). γ-carboxyglutamic acid residues of prothrombin were thermally decarboxylated following the method of Bajaj, S. P. et al. (1982), JBC 1982, Vol. 257, No. 7, 3726-3731. Biotinylated prothrombin as well as biotinylated decarboylated prothrombin were generated as follows: Prothrombin variants were dialysed against 100 mM $KPO_4$/100 mM KCl, pH 8.0, subsequently, pH was adjusted to pH 8.4, and the respective prothrombin variant was biotinylated using Biotin-DDS (Biotinoyl-amino-3,6-dioxaoctanyl-aminocarbonyl-heptanoic-acid-N-hydroxy succinimide ester (EP 0632810 B1)) at stoichiometry 1:2.75 (mol PT/mol Biotin-NHS-ester). After completion of the reaction, biotinylated prothrombin-variants were purified by size-exclusion chromatography on an Superdex 200 HR 10/30 column (GE Healthcare Life Sciences).

Antibodies binding their respective screening peptide were obtained by small scale expressions of clones (2 mL transfection of HEK-cells) and further evaluated as follows:

Firstly, the concentration of rabbit-IgG in the culture supernatant (20 µL sample volume) was determined employing a standard rabbit IgG sandwich ECL-immunoassay. In this assays 1 µg/mL biotinylated IgG sheep anti-rabbit Fcγ (75 µL) as well as 1 µg/mL ruthenylated sheep anti-rabbit Fcγ (70 µl), both in assay buffer (assay buffer comprises 40 mM $NaPO_4$, 150 mM NaCl, 5 mM EDTA, 0.1% (w/v) polydocanol, 2.0% (w/v) bovine plasma-albumine and has pH 7.5) and streptavidin coated magnetic beads (=Elecsys® beads) (35 µL; 0.7 mg/mL) are mixed and the sandwich formed is measured on an Elecsys 2010 (Roche Diagnostics, Germany) automated immunoanalyzer. The streptavidin coated magnetic beads (Elecsys® beads) used here are the same as the streptavidin coated magnetic beads contained in an Elecsys® reagents container as sold by Roche (Roche Diagnostics GmbH, Germany).

Based on the obtained result, supernatants were normalized with respect to rabbit IgG concentration, and reactivity to biotinylated descarboxy-prothrombin as well as cross-reactivity to biotinylated prothrombin was determined: Culture supernatants diluted to 50 ng/mL rabbit IgG (50 µL) were reacted with 75 ng/mL biotinylated descarboxy-prothrombin or prothrombin (50 µL), respectively, in a first step, and 1 µg/mL ruthenylated IgG sheep anti-rabbit Fcγ in assay buffer (s. above; 60 µL) and streptavidin coated magnetic Elecsys® beads (40 µL; 0.7 mg/mL) were used in the second incubation step. The sandwich complex formed was measured using an Elecsys 2010 automated immunoanalyzer. Only clones showing negligible cross-reactivity to native prothrombin were evaluated further.

Reactivity of this subset of clones to native PIVKA-II contained in human samples was investigated by analysing the degree of inhibition caused by the presence of diluted plasma of marcoumar-treated patients ("coumarin-plasma"), or plasma of patients suffering from hepatocellular carcinoma ("HCC-plasma"), in the descarboxy-prothrombin-binding assay described above: coumarin-plasma with INR>4 was obtained from Biomex GmbH, (Heidelberg, Germany). Culture supernatants diluted to 50 ng/mL rabbit IgG (20 µL) were reacted with coumarin plasma (1:25 in assay buffer) or solely assay buffer (reference) (40 µL) in a first step, and in analogy to the experiment described above, subsequently with 50 µL comprising 75 ng/mL biotinylated descarboxy-prothrombin and 55 µL of 1 µg/mL ruthenylated IgG sheep anti-rabbit Fcγ in assay buffer and streptavidin coated magnetic Elecsys® beads (35 µL; 0.7 mg/mL) using an Elecsys 2010 automated immuno analyzer. Analogously, culture supernatants (20 µL) were reacted with diluted HCC-plasma (1:3-1:160 in assay buffer, depending on the sample) or assay buffer (reference) (40 µL) as a first step, with following steps as described for the coumarin-plasma inhibition experiment. Relative reactivity of the clones to native PIVKA II was evaluated by calculating percent inhibition, i.e. the ratio of signals obtained in presence or absence (i.e. the reference condition) of native PIVKA-II.

Example 3

Influence of Carboxylation on Antibody Binding

For a detailed analysis of epitope-specificity of the selected clones with respect to the influence of gamma-carboxylation of defined glutamic acid residues in PIVKA-II, a set of biotinylated peptides was used (Table 2):

TABLE 2

Biotinylated PIVKA-II-Peptides without or with γ-carboxy-glutamate residues

| | Gla-Peptide | MW [g/mol] |
|---|---|---|
| Bi-SEQ ID NO: 1 | *H**Glu(Bi-PEG)*NLERECVEETCSYEEA*NH2 | 2457.65 |
| Bi-SEQ ID NO: 2 | *H**Glu(Bi-PEG)*NLERECVGlaETCSYEEA*NH2 | 2501.65 |
| Bi-SEQ ID NO: 4 | *H**Glu(Bi-PEG)*NLERECVEGlaTCSYEEA*NH2 | 2501.65 |
| Bi-SEQ ID NO: 3 | *H**Glu(Bi-PEG)*NLERECVEETCSYGlaEA*NH2 | 2501.65 |

For N-terminal biotinylation E(Biotin-PEG) (=Nδ-(N-biotinyl-3-(2-(2-(3-aminopropyloxy)-ethoxy)-ethoxypropyl)-L-glutamine) was used according to standard procedures. The N-terminal biotin-(linker)-tag is represented by *H**Glu(Bi-PEG)* in Table 2. *NH2 is used to illustrate that the C-terminal amino acid is present in the form of a C-terminal carboxamide.

An Elecsys 2010 immunoanalyzer was used to determine the reactivity of selected anti-PIVKA-II antibodies with the above peptide as follows:

50 µL of ruthenylated anti-PIVKA-II antibody (300 ng/mL in assay buffer—s. example 2.4) were reacted with 50 µL of biotinylated peptide (2.5 ng/mL in assay buffer) and 70 µL assay-buffer in a first step, and incubated at 37° C. for 9 min. After addition of 30 µL streptavidin coated paramagnetic Elecsys® beads (0.7 mg/mL; see example 2.4) and a second incubation step (37° C., 9 min), the reaction mixture was aspirated into the measuring cell where the microparticles are magnetically captured onto the surface of the measuring-electrode. Unbound substances are removed with ProCell system-buffer (Roche Diagnostics GmbH, Germany). Application of a voltage to the electrode then induces electrochemiluminescense-based emission of light which is measured by a photomultiplier.

The signals obtained with the various γ-carboxy-glutamate residue containing peptides (Bi-SEQ ID NO: 2, 3 and 4, respectively) were normalized to the reference peptide without any γ-carboxy-glutamate residue (Bi-SEQ ID NO:1).

TABLE 3

Reactivity of selected monoclonal antibodies against various iotinylated PIVKA-II-peptides

| Clone No. | SEQ ID NO: 1 (Reference) | Biotinylated peptide | | |
|---|---|---|---|---|
| | | SEQ ID NO: 2 | SEQ ID NO: 4 | SEQ ID NO: 3 |
| 13H7 | 100% | 5% | 68% | 107% |
| 7A10 | 100% | 4% | 68% | 105% |
| 9A6 | 100% | 5% | 78% | 107% |
| 4E8 | 100% | 5% | 76% | 108% |

As can be seen from Table 3, the presence of glutamic acid (absence of a γ-carboxylation of the glutamic acid residue) at position 19 of mature prothrombin (SEQ ID NO:6) is absolutely crucial for good antibody binding. The peptide of SEQ ID NO:2, biotinylated and otherwise treated exactly the same way as the reference peptide of SEQ ID NO:1 (having no γ-carboxy-glutamic acid residue at all), only yields about 5% of the signal that is obtained with the reference peptide. On the other hand and contrary to prior art antibodies, the antibodies according to the present disclosure—as exemplified in Table 3—bind to the peptide of SEQ ID NO:3 at least as good as to the peptide of SEQ ID NO:1.

Example 4

Sandwich Assay for Measurement of PIVKA-II 4.1 Production of Larger Quantities and Purification of Antibodies The pH of culture supernatants of 1 L transfections of HEK-cells was adjusted to pH 4.75 with 2 M acetic acid, and the solution was stirred for 20 min at room temperature. The turbid solution was cleared by centrifugation at ≥20 000×g for >20 min. Subsequently, the pH of the solution was readjusted to pH 7.5 by adding 2M $K_3PO_4$. Rabbit IgG was purified by affinity chromatography using MabSelect SuRe Protein A media: A 10 mL MabSelect SuRe™ Protein A column (GE Healthcare Life Sciences) was equilibrated with PBS (25 mM $KPO_4$, 150 mM KCl, pH 7.5), then, the clear culture supernatant was pumped over the column at flow rate 5-20 CV/h, followed by a first wash with PBS, a second wash with 130 mM $KPO_4$/15 mM Na-Citrate pH 6.5, and finally eluted using 0.14 M $KPO_4$, 15 mM Citrate, 0.1 M ammonium sulfate, pH 5.0. IgG-containing fractions were pooled, and the pH in the pool was readjusted to pH 7.5-8.0 using 2 M $K_3PO_4$. Finally the solution was dialysed against 50 mM $KPO_4$, 150 mM KCl, pH 7.5.

4.2 Biotinylation

To 1 mL solution of IgG (4.5 mg/mL in 100 mM $KPO_4$/150 mM KCl pH 8.4), 50 µL solution of Biotin-DDS (Biotinoyl-amino-3,6-dioxaoctanyl-aminocarbonyl-heptanoic-acid-N-hydroxy succinimide ester (EP 0632810 B1); 1.4 mg/ml in DMSO) are added (i.e. stoichiometry of 3 mol Biotin-NHS-ester per mol IgG). After 30 min stirring at room temperature, the derivatization was stopped by addition of 10 mM lysine. pH was adjusted to pH 7.5 with saturated $KH_2PO_4$, and the solution was dialysed against 50 mM $KPO_4$/150 mM KCl pH 7.4. For removal of aggregates, appropriate fractions were collected from size-exclusion chromatography on an Superdex 200 HR 10/30 column (GE Healthcare Life Sciences).

4.3 Ruthenylation

To 1 mL solution of IgG (4.5 mg/mL in 100 mM $KPO_4$/150 mM KCl pH 8.4), 50 µL solution of Ruthenate(3-), bis(2,2'-bipyridine-κN1,κN1')[N-[4-(4'-methyl[2,2'-bipyridin]-4-yl-κN1,κN1')-1-oxobutyl]-β-alanyl-L-α-glutamyl-L-α-glutamyl-N6-[8-[(2,5-dioxo-1-pyrrolidinyl)oxy]-1,8-dioxooctyl]-L-lysinato(3-)]-, (OC-6-33)-(9CI) (BPRu-UEEK-DSS; CAS 406218-59-5; 4.3 mg/ml in DMSO) are added (i.e. stoichiometry of 4.0 mol Ruthenium-NHS-ester per mol IgG). After 30 min stirring at room temperature, the derivatization was stopped by addition of 10 mM Lysine. pH was adjusted to pH 7.0 with saturated $KH_2PO_4$, and the reaction mixture was dialysed against 50 mM K—$PO_4$/0.15 M KCl/2% saccharose, pH 7.0. For removal of aggregates, appropriate fractions were collected from Size-exclusion chromatography on an Superdex 200 HR 10/30 column (GE Healthcare Life Sciences).

Example 5

Generation of Antibodies to the N-Terminus of PIVKA-II

Monoclonal antibodies to the N-terminus of PIVKA-II were also generated. In brief the peptide ANTFLEEVRKGNLERE-ßAla-Ahx-ßAla-Cys-NH2 (SEQ ID NO:34) was synthesized, comprising the amino acids 44 to 59 (SEQ ID NO:5) of preprothrombin as well as an N-terminal linker consisting of -ßAla-Ahx-ßAla-Cys-NH2. This linker comprises the amino acid derivatives ßAla=beta-alanine and Ahx=6-Aminohexanoic acid, respectively.

ESI-MS$_{calc}$: M$^+$=2262.6 Da;
ESI-MS$_{exp}$: [M+2H]$^{2+}$=1131.8 Da

To a solution of keyhole limpet hemocyanin (KLH) (150 mg) in phosphate buffer (45 mL, 20 mM, pH 7.2) 3-(Maleimido)propionic acid N-hydroxysuccinimide ester (55 mg, 207 mol dissolved in 1.5 mL dimethylsulfoxide (DMSO)) was added. The reaction mixture was incubated for 5 hours at room temperature and then dialyzed against phosphate buffer (0.1 M, pH 7.05). The peptide of (SEQ ID NO:34), comprising an N-terminal cysteine (6.8 mg, 3 µmol) was dissolved in DMSO and added to a solution of maleimide-activated KLH (36.7 mg) containing 0.1M EDTA. The solution was agitated for 5 hours at room temperature and then dialyzed against phosphate buffer (0.1 M, pH 7.05) to yield 28 mg KLH-peptide conjugate.

Thereafter antibodies generated by aid of this immunogen were obtained according to standard procedures.

Example 6

General Description of the Elecsys Sandwich Assay

Figure 1:
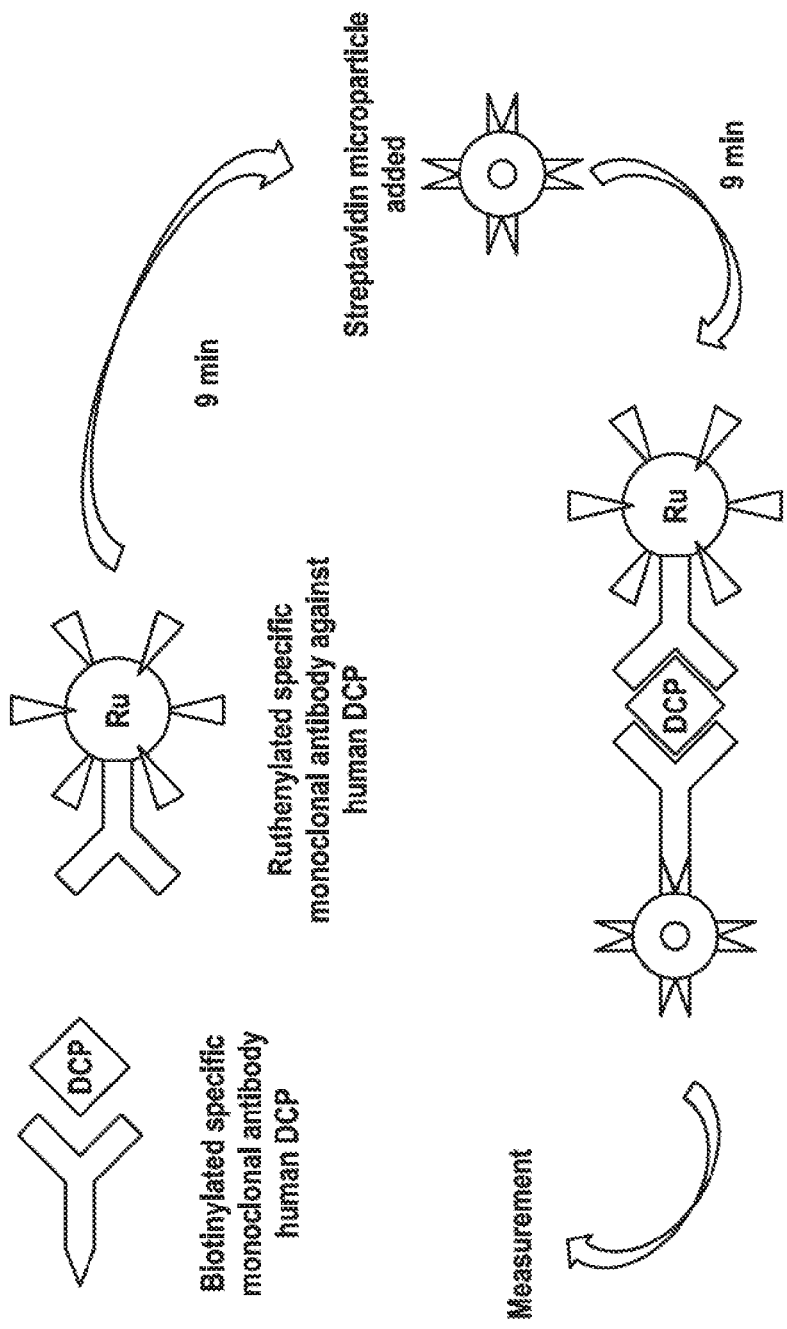
FIG. 1: Schematic to the PIVKA-II immuno assay on Elecsys

The test principle of the immunological sandwich assay is depicted in FIG. 1. The total incubation time required for the assay is 18 minutes.

$1^{st}$ incubation (9 min): 20 μL of a sample (1:5 pre-diluted), $1^{st}$ biotinylated monoclonal PIVKA-II-specific antibody to the N-terminus of PIVKA-II), and the $2^{nd}$ PIVKA-II-specific monoclonal antibody (7A10) labeled according to Example 4 with ruthenium complex are co-incubated and form a sandwich complex comprising the biotinylated antibody, PIVKA-II and the ruthenylated antibody $2^{nd}$ incubation (9 min): Streptavidin-coated microparticles (Elecsys® beads) are added to the mixture of the first incubation step and during this second incubation the complex comprising the biotinylated antibody, PIVKA-II and the ruthenylated antibody becomes bound to the solid phase via interaction of biotin and streptavidin The reaction mixture is aspirated into the measuring cell where the microparticles are magnetically captured onto the surface of the electrode. Unbound substances are then removed with ProCell II M. Application of a voltage to the electrode then induces electrochemiluminescense-based emission of light which is measured by a photomultiplier As is standard and routine, PIVKA-II is then quantified/measured via a calibration curve.

The measuring range of newly developed PIVKA-II Elecsys® assay is 0-5000 ng/ml

Example 7

Application of PIVKA-II Elecsys Assay in the Early Detection of Hepatocellular Carcinoma (HCC)

7.1 Analyzed Samples

PIVKA-II levels were examined in the sera collected from patients and controls within a prospective multi-center sample collection.

The composition of the sample panel was as follows:
Patients:
Hepatocellular carcinoma (HCC) (n=309), including:
BCLC (Barcelona Clinic Liver Cancer) stages 0 (n=10), BCLC A (n=116), BCLC B (n=77), BCLC C (n=82), BCLC D: (n=12); Patients with no staging (n=12), Other patients CCC (=Cholangiocarcinoma) and mixed HCC/CCC (n=21), Controls:

In total 742 samples from control subjects have been obtained, including chronic Hepatitis B infection (HBV) patients (n=226), chronic Hepatitis C infection (HCV) patients (n=52), cirrhosis+HBV (n=173), cirrhosis+HCV (n=136), cirrhosis mixed (n=88), other (n=67). Another group of control subjects comprises suspicious but not further clarified cases (n=12).

Origin of Samples:

Samples have been collected at the following sites: (1) Thailand: Songklanagarind Hospital Hat Yai; Srinagarind Hospital Khon Kaen; Siriraj Hospital Bangkok; Maharaj Nakorn Hospital Chiang Mai; (2) China: Prince of Wales Hospital, Hong Kong; (3) Germany: NCT Heidelberg; (4) Spain: Hospital Vall d'Hebron Barcelona

TABLE 4

Demographic information on the samples collected/analyzed

| | All (N = 1084) | Thailand (N = 725) | China (N = 189) | Germany (N = 90) | Spain (N = 80) |
|---|---|---|---|---|---|
| Age [years] (SD) | 57.2 ± 10.8 | 55.6 ± 10.2 | 58.5 ± 11.1 | 63.2 ± 10.2 | 61.6 ± 12.4 |
| Sex male (%) | 684 (63.1) | 433 (59.7) | 144 (76.2) | 65 (72.2) | 42 (52.5) |
| Race (%) | | | | | |
| Asian | 902 (83.2) | 712 (98.2) | 189 (100) | 0 | 1 (1.3) |
| Caucasian/white | 166 (15.3) | 1 (0.1) | 0 | 88 (97.78) | 77 (96.3) |

7.2 Method Comparison of the Elecsys PIVKA-II Assay to WAKO DCP Test

Serum samples (n=1084) described in 7.1 were analyzed by PIVKA-II Elecsys assay and WAKO DCP assay (WAKO Chemicals GmbH, Fuggerstr. 12, D-41 468 Neuss, Germany).

WAKO DCP assay is based on microfluidic isotachophoresis of antibody-bound DCP detected with laser-induced fluorescence and applies one specific antibody raised against aa11-35 of prothrombin (YS5; Yamaguchi et al., Clin. Chem. Lab. Med. 2008; 46(3): 411-6). The reportable range of WAKO DCP test is 0.1-950 ng/ml.

Coefficient of linear correlation (FIG. 2) is below 0.9, indicating differences in recognition of the native PIVKA-II in the samples analyzed. It is assumed that the reasons for the weak correlation between WAKO and the Elecsys assay disclosed herein above lies in the recognition of different PIVKA-II forms due to the different antibody binding of the capture antibody according to the present invention 7.3. Comparison of the Clinical Performance of the Elecsys PIVKA-II Assay as Compared to the WAKO DCP (PIVKA-II) Test The clinical sensitivity for Roche PIVKA-II and WAKO DCP assays was calculated at 90% specificity. In parallel, clinical specificity for Roche PIVKA-II and WAKO DCP assays was calculated at 90% sensitivity. Independent evaluations were performed for all stages HCC (n=309) vs. all controls and early stages HCC (BCLC 0 and A, n=126) vs. all controls. Additionally, the area under the curve (AUC) was calculated for both assays and evaluation methods.

TABLE 5

Clinical performance characteristics for the PIVKA-II Elecsys assay and for WAKO DCP assay Optimized cutoffs

|  |  | Elecsys PIVKA-II | WAKO DCP |
|---|---|---|---|
| All HCC | AUC | 0.89 | 0.88 |
|  | Sensitivity @90 Spec | 78% (73%-82.5%) | 78% (73%-82.5%) |
|  | Specificity @90 Sens | 59% (55.3%-62.5%) | 61% (48%-66.3%) |
| Early stages HCC (BCLC 0 and A) | AUC | 0.79 | 0.77 |
|  | Sensitivity @90 Spec | 55.6% (46.4%-64.4%) | 56.3% (47.2%-65.2%) |
|  | Specificity @90 Sens | 27.6% (24.4%-31%) | 26.1% (22.9%-29.4%) |

As can be seen from Table 5, the clinical specificity at cut-off optimized for 90% sensitivity for all HCC stages vs. controls as well as for early stages HCC vs controls of Elecsys PIVKA-II assay is superior as compared to the WAKO DCP test (59% vs. 51% and 27.6% vs 26.1%, respectively).

At the same time the sensitivity at cut-off optimized for 90% specificity is very comparable for both assays.

The Elecsys PIVKA-II assay also shows a slightly increased AUC calculated for both all HCC and early stages HCC groups, respectively, versus controls. Detailed analysis of receiver operator curve (ROC) in the high sensitivity area (60-95%) confirms superior specificity of Elecsys PIVKA-II vs. WAKO DCP for all HCC stages (FIG. 3) and early HCC stages (FIG. 4), respectively.

7.4. Conclusion

Since false-positive rates of existing PIVKA-II assays are still significant (Lee et al. Korean J. Clin. Pathol. 1997; 17(3): 395-404, Taketa et al. Acta Med. Okayama 2002; 56 (6): 317-320) and since the sensitivity and specificity in the detection of early stages of HCC is not as good as for late stages HCC (Lim et al. Scand. J. Gastroenterol. 2016; 51(3): 344-53), improvements of PIVKA-II detection methods are of high importance in clinical decision making. As disclosed herein, the use of an antibody with unique binding properties around the γ-carboxylated amino acids 19 and 20, respectively, of PIVKA-II results in an improved specificity of this newly developed PIVKA-II assay, especially in high sensitivity region. This holds true, for both, detection of all HCC patients as well as even for detection of early stages (BCLC 0-A) of HCC.

The invention claimed is:

1. A composition comprising an antibody containing CDRs that comprise the following amino acid sequences:
   (i) a CDR1 comprising the amino acid sequence of SEQ ID NO:10, a CDR2 comprising the amino acid sequence of SEQ ID NO:11, and a CDR3 comprising the amino acid sequence of SEQ ID NO:12 in the light chain variable domain, and a CDR1 comprising the amino acid sequence of SEQ ID NO:13, a CDR2 comprising the amino acid sequence of SEQ ID NO:14, and a CDR3 comprising the amino acid sequence of SEQ ID NO:15 in the heavy chain variable domain;
   (ii) a CDR1 comprising the amino acid sequence of SEQ ID NO:18, a CDR2 comprising the amino acid sequence of SEQ ID NO:19, and a CDR3 comprising the amino acid sequence of SEQ ID NO:20 in the light chain variable domain, and a CDR1 comprising the amino acid sequence of SEQ ID NO:21, a CDR2 comprising the amino acid sequence of SEQ ID NO:22, and a CDR3 comprising the amino acid sequence of SEQ ID NO:15 in the heavy chain variable domain;
   (iii) a CDR1 comprising the amino acid sequence of SEQ ID NO:18, a CDR2 comprising the amino acid sequence of SEQ ID NO:11, and a CDR3 comprising the amino acid sequence of SEQ ID NO:20 in the light chain variable domain, and a CDR1 comprising the amino acid sequence of SEQ ID NO:21, a CDR2 comprising the amino acid sequence of SEQ ID NO:25, and a CDR3 comprising the amino acid sequence of SEQ ID NO:15 in the heavy chain variable domain; or
   (iv) a CDR1 comprising the amino acid sequence of SEQ ID NO:18, a CDR2 comprising the amino acid sequence of SEQ ID NO:11, and a CDR3 comprising the amino acid sequence of SEQ ID NO:28 in the light chain variable domain, and a CDR1 comprising the amino acid sequence of SEQ ID NO:29, a CDR2 comprising the amino acid sequence of SEQ ID NO:25, and a CDR3 comprising the amino acid sequence of SEQ ID NO:15 in the heavy chain variable domain.

2. The composition of claim 1, wherein the antibody is a monoclonal antibody.

3. The composition of claim 1, wherein the antibody binds to a synthetic peptide of SEQ ID NO:1, has an at least 10-fold binding preference for the peptide of SEQ ID NO:1 as compared to a synthetic peptide of SEQ ID NO:2 and binds to a synthetic peptide of SEQ ID NO:3 at least as good as compared to the peptide of SEQ ID NO:1.

4. The composition of claim 3, wherein the antibody also has a binding preference for a peptide of SEQ ID NO:1 as compared to a peptide of SEQ ID NO:4.

5. The composition of claim 1, wherein the antibody binds to a synthetic peptide of SEQ ID NO:1 has an at least 15-fold binding preference for the peptide of SEQ ID NO:1 as compared to a synthetic peptide of SEQ ID NO: 2.

6. The composition of claim 5, wherein the antibody also has a binding preference for a peptide of SEQ ID NO:1 as compared to a peptide of SEQ ID NO:4.

7. The composition of claim 1, wherein the antibody is a specific binding agent binding to PIVKA-II.

8. A method of detecting PIVKA-II in a sample, the method comprising the steps of:
   a) contacting the sample with the antibody according to claim 1 for a time and under conditions sufficient for the formation of antibody-PIVKA-II complex; and b) detecting the presence of the antibody-PIVKA-II complex, wherein the presence of the antibody-PIVKA-II complex indicates the presence of PIVKA-II in the sample.

9. The method of claim 8 wherein
step a) further comprises contacting the sample with a second specific binding agent to PIVKA-II, wherein the second specific binding agent is detectably labeled, for a time and under conditions sufficient to form an antibody-PIVKA-II-second specific binding agent complex; and wherein
step b) comprises measuring the complex formed in (a), thereby detecting PIVKA-II in the sample.

10. The method according to claim 9, wherein the second specific binding agent is a polyclonal or a monoclonal antibody.

11. The method according to claim 9, wherein the epitope on PIVKA-II bound by the second specific binding agent is comprised within F1/F2.

12. The method according to claim 9, wherein the epitope on PIVKA-II bound by the second specific binding agent is comprised within F1.

13. The method according to claim 9, wherein the epitope on PIVKA-II bound by the second specific binding agent is comprised within the Gla-domain of PIVKA-II.

14. A method of diagnosing HCC in a patient suspected of having HCC, comprising the steps of:
a) obtaining a sample from the patient;
b) contacting the sample with a first specific binding agent to PIVKA-II according to claim 1 and a second specific binding agent to PIVKA-II, wherein the second specific binding agent is detectably labeled, for a time and under conditions sufficient to form a first specific binding agent-PIVKA-II-second specific binding agent complex;
c) measuring the complex formed in (b), thereby measuring the amount of PIVKA-II present in the sample, wherein an amount of PIVKA-II greater than a reference level is indicative of the presence of HCC in the patient.

* * * * *

```
                      SEQUENCE LISTING

<160> NUMBER OF SEQ ID NOS: 34

<210> SEQ ID NO 1
<211> LENGTH: 16
<212> TYPE: PRT
<213> ORGANISM: Artificial Sequence
<220> FEATURE:
<223> OTHER INFORMATION: synthetic peptide

<400> SEQUENCE: 1

Asn Leu Glu Arg Glu Cys Val Glu Glu Thr Cys Ser Tyr Glu Glu Ala
1               5                   10                  15

<210> SEQ ID NO 2
<211> LENGTH: 16
<212> TYPE: PRT
<213> ORGANISM: Artificial sequence
<220> FEATURE:
<223> OTHER INFORMATION: synthetic peptide
<220> FEATURE:
<221> NAME/KEY: Xaa
<222> LOCATION: (8)..(8)
<223> OTHER INFORMATION: Xaa is gamma-carboxylated glutamic acid

<400> SEQUENCE: 2

Asn Leu Glu Arg Glu Cys Val Xaa Glu Thr Cys Ser Tyr Glu Glu Ala
1               5                   10                  15

<210> SEQ ID NO 3
<211> LENGTH: 16
<212> TYPE: PRT
<213> ORGANISM: Artificial sequence
<220> FEATURE:
<223> OTHER INFORMATION: synthetic peptide
<220> FEATURE:
<221> NAME/KEY: Xaa
<222> LOCATION: (13)..(13)
```

```
<223> OTHER INFORMATION: Xaa represents gamma carboxylated glutamic acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 3

Asn Leu Glu Arg Glu Cys Val Glu Glu Thr Cys Ser Tyr Xaa Glu Ala
1               5                   10                  15

<210> SEQ ID NO 4
<211> LENGTH: 16
<212> TYPE: PRT
<213> ORGANISM: Artificial sequence
<220> FEATURE:
<223> OTHER INFORMATION: synthetic peptide
<220> FEATURE:
<221> NAME/KEY: Xaa
<222> LOCATION: (9)..(9)
<223> OTHER INFORMATION: Xaa represents gamma carboxylated glutamic acid

<400> SEQUENCE: 4

Asn Leu Glu Arg Glu Cys Val Glu Xaa Thr Cys Ser Tyr Glu Glu Ala
1               5                   10                  15

<210> SEQ ID NO 5
<211> LENGTH: 622
<212> TYPE: PRT
<213> ORGANISM: Homo sapiens

<400> SEQUENCE: 5

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
                20                  25                  30

Gln Ala Arg Ser Leu Leu Gln Arg Val Arg Arg Ala Asn Thr Phe Leu
            35                  40                  45

Glu Glu Val Arg Lys Gly Asn Leu Glu Arg Glu Cys Val Glu Glu Thr
        50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
```

```
            225                 230                 235                 240

Gln Ala Lys Ala Leu Ser Lys His Gln Asp Phe Asn Ser Ala Val Gln
                        245                 250                 255

Leu Val Glu Asn Phe Cys Arg Asn Pro Asp Gly Asp Glu Glu Gly Val
                        260                 265                 270

Trp Cys Tyr Val Ala Gly Lys Pro Gly Asp Phe Gly Tyr Cys Asp Leu
                        275                 280                 285

Asn Tyr Cys Glu Glu Ala Val Glu Glu Thr Gly Asp Gly Leu Asp
                    290                 295                 300

Glu Asp Ser Asp Arg Ala Ile Glu Gly Arg Thr Ala Thr Ser Glu Tyr
        305                 310                 315                 320

Gln Thr Phe Phe Asn Pro Arg Thr Phe Gly Ser Gly Glu Ala Asp Cys
                        325                 330                 335

Gly Leu Arg Pro Leu Phe Glu Lys Lys Ser Leu Glu Asp Lys Thr Glu
                        340                 345                 350

Arg Glu Leu Leu Glu Ser Tyr Ile Asp Gly Arg Ile Val Glu Gly Ser
                        355                 360                 365

Asp Ala Glu Ile Gly Met Ser Pro Trp Gln Val Met Leu Phe Arg Lys
                    370                 375                 380

Ser Pro Gln Glu Leu Leu Cys Gly Ala Ser Leu Ile Ser Asp Arg Trp
        385                 390                 395                 400

Val Leu Thr Ala Ala His Cys Leu Leu Tyr Pro Pro Trp Asp Lys Asn
                        405                 410                 415

Phe Thr Glu Asn Asp Leu Leu Val Arg Ile Gly Lys His Ser Arg Thr
                        420                 425                 430

Arg Tyr Glu Arg Asn Ile Glu Lys Ile Ser Met Leu Glu Lys Ile Tyr
                    435                 440                 445

Ile His Pro Arg Tyr Asn Trp Arg Glu Asn Leu Asp Arg Asp Ile Ala
                    450                 455                 460

Leu Met Lys Leu Lys Lys Pro Val Ala Phe Ser Asp Tyr Ile His Pro
        465                 470                 475                 480

Val Cys Leu Pro Asp Arg Glu Thr Ala Ala Ser Leu Leu Gln Ala Gly
                        485                 490                 495

Tyr Lys Gly Arg Val Thr Gly Trp Gly Asn Leu Lys Glu Thr Trp Thr
                        500                 505                 510

Ala Asn Val Gly Lys Gly Gln Pro Ser Val Leu Gln Val Val Asn Leu
                        515                 520                 525

Pro Ile Val Glu Arg Pro Val Cys Lys Asp Ser Thr Arg Ile Arg Ile
        530                 535                 540

Thr Asp Asn Met Phe Cys Ala Gly Tyr Lys Pro Asp Glu Gly Lys Arg
        545                 550                 555                 560

Gly Asp Ala Cys Glu Gly Asp Ser Gly Gly Pro Phe Val Met Lys Ser
                        565                 570                 575

Pro Phe Asn Asn Arg Trp Tyr Gln Met Gly Ile Val Ser Trp Gly Glu
                        580                 585                 590

Gly Cys Asp Arg Asp Gly Lys Tyr Gly Phe Tyr Thr His Val Phe Arg
                    595                 600                 605

Leu Lys Lys Trp Ile Gln Lys Val Ile Asp Gln Phe Gly Glu
                610                 615                 620

<210> SEQ ID NO 6
<211> LENGTH: 579
<212> TYPE: PRT
<213> ORGANISM: Homo sapiens
```

<400> SEQUENCE: 6

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg Ser Glu Gly Ser Ser
145                 150                 155                 160

Val Asn Leu Ser Pro Pro Leu Glu Gln Cys Val Pro Asp Arg Gly Gln
                165                 170                 175

Gln Tyr Gln Gly Arg Leu Ala Val Thr Thr His Gly Leu Pro Cys Leu
            180                 185                 190

Ala Trp Ala Ser Ala Gln Ala Lys Ala Leu Ser Lys His Gln Asp Phe
        195                 200                 205

Asn Ser Ala Val Gln Leu Val Glu Asn Phe Cys Arg Asn Pro Asp Gly
    210                 215                 220

Asp Glu Glu Gly Val Trp Cys Tyr Val Ala Gly Lys Pro Gly Asp Phe
225                 230                 235                 240

Gly Tyr Cys Asp Leu Asn Tyr Cys Glu Glu Ala Val Glu Glu Glu Thr
                245                 250                 255

Gly Asp Gly Leu Asp Glu Asp Ser Asp Arg Ala Ile Glu Gly Arg Thr
            260                 265                 270

Ala Thr Ser Glu Tyr Gln Thr Phe Phe Asn Pro Arg Thr Phe Gly Ser
        275                 280                 285

Gly Glu Ala Asp Cys Gly Leu Arg Pro Leu Phe Glu Lys Lys Ser Leu
    290                 295                 300

Glu Asp Lys Thr Glu Arg Glu Leu Leu Glu Ser Tyr Ile Asp Gly Arg
305                 310                 315                 320

Ile Val Glu Gly Ser Asp Ala Glu Ile Gly Met Ser Pro Trp Gln Val
                325                 330                 335

Met Leu Phe Arg Lys Ser Pro Gln Glu Leu Leu Cys Gly Ala Ser Leu
            340                 345                 350

Ile Ser Asp Arg Trp Val Leu Thr Ala Ala His Cys Leu Leu Tyr Pro
        355                 360                 365

Pro Trp Asp Lys Asn Phe Thr Glu Asn Asp Leu Leu Val Arg Ile Gly
    370                 375                 380

Lys His Ser Arg Thr Arg Tyr Glu Arg Asn Ile Glu Lys Ile Ser Met
385                 390                 395                 400

Leu Glu Lys Ile Tyr Ile His Pro Arg Tyr Asn Trp Arg Glu Asn Leu

```
                    405                 410                 415
Asp Arg Asp Ile Ala Leu Met Lys Leu Lys Pro Val Ala Phe Ser
            420                 425                 430

Asp Tyr Ile His Pro Val Cys Leu Pro Asp Arg Glu Thr Ala Ala Ser
        435                 440                 445

Leu Leu Gln Ala Gly Tyr Lys Gly Arg Val Thr Gly Trp Gly Asn Leu
    450                 455                 460

Lys Glu Thr Trp Thr Ala Asn Val Gly Lys Gly Gln Pro Ser Val Leu
465                 470                 475                 480

Gln Val Val Asn Leu Pro Ile Val Glu Arg Pro Val Cys Lys Asp Ser
                485                 490                 495

Thr Arg Ile Arg Ile Thr Asp Asn Met Phe Cys Ala Gly Tyr Lys Pro
            500                 505                 510

Asp Glu Gly Lys Arg Gly Asp Ala Cys Glu Gly Asp Ser Gly Gly Pro
        515                 520                 525

Phe Val Met Lys Ser Pro Phe Asn Asn Arg Trp Tyr Gln Met Gly Ile
    530                 535                 540

Val Ser Trp Gly Glu Gly Cys Asp Arg Asp Gly Lys Tyr Gly Phe Tyr
545                 550                 555                 560

Thr His Val Phe Arg Leu Lys Lys Trp Ile Gln Lys Val Ile Asp Gln
                565                 570                 575

Phe Gly Glu

<210> SEQ ID NO 7
<211> LENGTH: 46
<212> TYPE: PRT
<213> ORGANISM: Homo sapiens

<400> SEQUENCE: 7

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
                20                  25                  30

Ser Ser Thr Ala Thr Asp Val Phe Trp Ala Lys Tyr Thr Ala
            35                  40                  45

<210> SEQ ID NO 8
<211> LENGTH: 225
<212> TYPE: PRT
<213> ORGANISM: Homo sapiens

<400> SEQUENCE: 8

Cys Glu Thr Ala Arg Thr Pro Arg Asp Lys Leu Ala Ala Cys Leu Glu
1               5                   10                  15

Gly Asn Cys Ala Glu Gly Leu Gly Thr Asn Tyr Arg Gly His Val Asn
                20                  25                  30

Ile Thr Arg Ser Gly Ile Glu Cys Gln Leu Trp Arg Ser Arg Tyr Pro
            35                  40                  45

His Lys Pro Glu Ile Asn Ser Thr Thr His Pro Gly Ala Asp Leu Gln
        50                  55                  60

Glu Asn Phe Cys Arg Asn Pro Asp Ser Ser Thr Thr Gly Pro Trp Cys
65                  70                  75                  80

Tyr Thr Thr Asp Pro Thr Val Arg Arg Gln Glu Cys Ser Ile Pro Val
                85                  90                  95

Cys Gly Gln Asp Gln Val Thr Val Ala Met Thr Pro Arg Ser Glu Gly
            100                 105                 110
```

Ser Ser Val Asn Leu Ser Pro Leu Glu Gln Cys Val Pro Asp Arg
            115                 120                 125

Gly Gln Gln Tyr Gln Gly Arg Leu Ala Val Thr Thr His Gly Leu Pro
    130                 135                 140

Cys Leu Ala Trp Ala Ser Ala Gln Ala Lys Ala Leu Ser Lys His Gln
145                 150                 155                 160

Asp Phe Asn Ser Ala Val Gln Leu Val Glu Asn Phe Cys Arg Asn Pro
                165                 170                 175

Asp Gly Asp Glu Glu Gly Val Trp Cys Tyr Val Ala Gly Lys Pro Gly
            180                 185                 190

Asp Phe Gly Tyr Cys Asp Leu Asn Tyr Cys Glu Glu Ala Val Glu Glu
            195                 200                 205

Glu Thr Gly Asp Gly Leu Asp Glu Asp Ser Asp Arg Ala Ile Glu Gly
    210                 215                 220

Arg
225

<210> SEQ ID NO 9
<211> LENGTH: 155
<212> TYPE: PRT
<213> ORGANISM: Homo sapiens

<400> SEQUENCE: 9

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg
145                 150                 155

<210> SEQ ID NO 10
<211> LENGTH: 11
<212> TYPE: PRT
<213> ORGANISM: Mus musculus

<400> SEQUENCE: 10

Gln Ala Ser Gln Ser Ile Gly Asn Asn Leu Ala
1               5                   10

<210> SEQ ID NO 11
<211> LENGTH: 7
<212> TYPE: PRT
<213> ORGANISM: Mus musculus

<400> SEQUENCE: 11

Ser Ala Ser Thr Leu Ala Ser
1               5

<210> SEQ ID NO 12
<211> LENGTH: 14
<212> TYPE: PRT
<213> ORGANISM: Mus musculus

<400> SEQUENCE: 12

Gln Ser Tyr Ala Gly Val Ser Glu Ser Val Phe Trp Tyr Ser
1               5                   10

<210> SEQ ID NO 13
<211> LENGTH: 13
<212> TYPE: PRT
<213> ORGANISM: Mus musculus

<400> SEQUENCE: 13

Thr Val Ser Gly Ile Asp Leu Ser Thr Tyr Ala Met Gly
1               5                   10

<210> SEQ ID NO 14
<211> LENGTH: 16
<212> TYPE: PRT
<213> ORGANISM: Mus musculus

<400> SEQUENCE: 14

Ile Ile Arg Ser Ser Gly Arg Thr Tyr Tyr Ala Ser Trp Ala Lys Gly
1               5                   10                  15

<210> SEQ ID NO 15
<211> LENGTH: 4
<212> TYPE: PRT
<213> ORGANISM: Mus musculus

<400> SEQUENCE: 15

Asn Val Ser Leu
1

<210> SEQ ID NO 16
<211> LENGTH: 112
<212> TYPE: PRT
<213> ORGANISM: Mus musculus

<400> SEQUENCE: 16

Asp Val Val Met Thr Gln Thr Pro Ser Ser Val Glu Ala Ala Val Gly
1               5                   10                  15

Gly Thr Val Thr Ile Lys Cys Gln Ala Ser Gln Ser Ile Gly Asn Asn
            20                  25                  30

Leu Ala Trp Tyr Gln Gln Lys Pro Gly Gln Arg Pro Asn Leu Leu Ile
        35                  40                  45

Tyr Ser Ala Ser Thr Leu Ala Ser Gly Val Pro Ser Arg Phe Arg Gly
    50                  55                  60

Ser Gly Ser Gly Thr Glu Phe Thr Leu Thr Ile Ser Gly Val Gln Cys
65                  70                  75                  80

Asp Asp Ala Ala Thr Tyr Tyr Cys Gln Ser Tyr Ala Gly Val Ser Glu
                85                  90                  95

Ser Val Phe Trp Tyr Ser Phe Gly Gly Thr Gly Val Val Lys
            100                 105                 110

<210> SEQ ID NO 17
<211> LENGTH: 110
<212> TYPE: PRT
<213> ORGANISM: Mus musculus

<400> SEQUENCE: 17

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Tyr Ala
            20                  25                  30

Met Gly Trp Val Arg Gln Ala Pro Gly Lys Gly Leu Glu Tyr Ile Gly
        35                  40                  45

Ile Ile Arg Ser Ser Gly Arg Thr Tyr Tyr Ala Ser Trp Ala Lys Gly
    50                  55                  60

Arg Phe Thr Val Ser Lys Thr Ser Thr Thr Val Asp Leu Ser Met
65                  70                  75                  80

Thr Ser Pro Thr Glu Asp Thr Ala Thr Tyr Tyr Cys Tyr Arg Asn
                85                  90                  95

Val Ser Leu Trp Gly Gln Gly Thr Leu Val Ser Val Ser Ser
            100                 105                 110

<210> SEQ ID NO 18
<211> LENGTH: 11
<212> TYPE: PRT
<213> ORGANISM: Mus musculus

<400> SEQUENCE: 18

Gln Ala Ser Gln Ser Ile Gly Ser Asn Leu Ala
1               5                   10

<210> SEQ ID NO 19
<211> LENGTH: 7
<212> TYPE: PRT
<213> ORGANISM: Mus musculus

<400> SEQUENCE: 19

Ser Ala Ser Thr Leu Ala Pro
1               5

<210> SEQ ID NO 20
<211> LENGTH: 14
<212> TYPE: PRT
<213> ORGANISM: Mus musculus

<400> SEQUENCE: 20

Gln Ser Tyr Ala Gly Val Ser Ala Asn Ile Phe Tyr Tyr Ser
1               5                   10

<210> SEQ ID NO 21
<211> LENGTH: 13
<212> TYPE: PRT
<213> ORGANISM: Mus musculus

<400> SEQUENCE: 21

Thr Val Ser Gly Phe Asp Leu Ser Arg Tyr Ala Val Gly
1               5                   10

<210> SEQ ID NO 22
<211> LENGTH: 16
<212> TYPE: PRT
<213> ORGANISM: Mus musculus -continued

<400> SEQUENCE: 22

Leu Ile Thr Ser Asp Gly Arg Thr Tyr Tyr Ala Asn Trp Ala Lys Gly
1               5                   10                  15

<210> SEQ ID NO 23
<211> LENGTH: 112
<212> TYPE: PRT
<213> ORGANISM: Mus musculus

<400> SEQUENCE: 23

Asp Val Val Met Thr Gln Thr Pro Ala Ser Val Glu Ala Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Ser Gly Gln Pro Pro Lys Leu Leu Ile
        35                  40                  45

Tyr Ser Ala Ser Thr Leu Ala Pro Gly Val Ser Ser Arg Phe Ser Gly
    50                  55                  60

Ser Gly Ser Gly Thr Glu Phe Thr Leu Thr Phe Thr Gly Val Gln Cys
65                  70                  75                  80

Gly Asp Ala Ala Thr Tyr Phe Cys Gln Ser Tyr Ala Gly Val Ser Ala
                85                  90                  95

Asn Ile Phe Tyr Tyr Ser Phe Gly Gly Gly Thr Glu Val Val Val Met
            100                 105                 110

<210> SEQ ID NO 24
<211> LENGTH: 110
<212> TYPE: PRT
<213> ORGANISM: Mus musculus

<400> SEQUENCE: 24

Gln Ser Val Glu Glu Ser Gly Gly Arg Leu Val Thr Pro Gly Thr Pro
1               5                   10                  15

Leu Thr Leu Thr Cys Thr Val Ser Gly Phe Asp Leu Ser Arg Tyr Ala
            20                  25                  30

Val Gly Trp Val Arg Gln Ala Pro Gly Lys Gly Leu Glu Tyr Ile Gly
        35                  40                  45

Leu Ile Thr Ser Asp Gly Arg Thr Tyr Tyr Ala Asn Trp Ala Lys Gly
    50                  55                  60

Arg Phe Thr Val Ser Lys Thr Ser Ser Thr Thr Val Asp Leu Lys Met
65                  70                  75                  80

Thr Ser Pro Thr Thr Glu Asp Thr Ala Thr Tyr Tyr Cys Tyr Arg Asn
                85                  90                  95

Val Ser Leu Trp Gly Gln Gly Thr Leu Val Ser Val Ser Ser
            100                 105                 110

<210> SEQ ID NO 25
<211> LENGTH: 16
<212> TYPE: PRT
<213> ORGANISM: Mus musculus

<400> SEQUENCE: 25

Leu Ile Val Ser Asp Gly Arg Thr Tyr Tyr Ala Ser Trp Ala Lys Gly
1               5                   10                  15

<210> SEQ ID NO 26
<211> LENGTH: 112
<212> TYPE: PRT
<213> ORGANISM: Mus musculus

```
<400> SEQUENCE: 26

Asp Val Val Met Thr Gln Thr Pro Ser Ser Val Glu Ala Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Glu Phe Thr Leu Thr Phe Ser Gly Val Gln Cys
65                  70                  75                  80

Gly Asp Ala Ala Thr Tyr Phe Cys Gln Ser Tyr Ala Gly Val Ser Ala
                85                  90                  95

Asn Ile Phe Tyr Tyr Ser Phe Gly Gly Gly Thr Glu Val Val Val Met
            100                 105                 110

<210> SEQ ID NO 27
<211> LENGTH: 110
<212> TYPE: PRT
<213> ORGANISM: Mus musculus

<400> SEQUENCE: 27

Gln Ser Val Glu Glu Ser Gly Gly Arg Leu Ile Thr Pro Gly Thr Pro
1               5                   10                  15

Leu Thr Leu Thr Cys Thr Val Ser Gly Phe Asp Leu Ser Arg Tyr Ala
            20                  25                  30

Val Gly Trp Val Arg Gln Ala Pro Gly Lys Gly Leu Glu Tyr Ile Gly
        35                  40                  45

Leu Ile Val Ser Asp Gly Arg Thr Tyr Tyr Ala Ser Trp Ala Lys Gly
    50                  55                  60

Arg Phe Thr Val Ser Lys Thr Ser Ser Thr Thr Val Asp Leu Lys Met
65                  70                  75                  80

Thr Ser Pro Thr Ala Gly Asp Thr Ala Thr Tyr Tyr Cys Tyr Arg Asn
                85                  90                  95

Val Ser Leu Trp Gly Gln Gly Thr Leu Val Ser Val Ser Ser
            100                 105                 110

<210> SEQ ID NO 28
<211> LENGTH: 14
<212> TYPE: PRT
<213> ORGANISM: Mus musculus

<400> SEQUENCE: 28

Gln Ser Tyr Ala Gly Ile Ser Ala Asn Ile Phe Tyr Tyr Ala
1               5                   10

<210> SEQ ID NO 29
<211> LENGTH: 13
<212> TYPE: PRT
<213> ORGANISM: Mus musculus

<400> SEQUENCE: 29

Thr Val Ser Gly Phe Asp Leu Ser Arg Tyr Ala Met Gly
1               5                   10

<210> SEQ ID NO 30
<211> LENGTH: 112
<212> TYPE: PRT
```

<213> ORGANISM: Mus musculus

<400> SEQUENCE: 30

Asp Val Val Met Thr Gln Thr Pro Ser Ser Val Glu Ala Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Ser Ser Arg Phe Lys Gly
50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Ala Gly Ile Ser Ala
                85                  90                  95

Asn Ile Phe Tyr Tyr Ala Phe Gly Gly Gly Thr Glu Val Val Val Met
            100                 105                 110

<210> SEQ ID NO 31
<211> LENGTH: 110
<212> TYPE: PRT
<213> ORGANISM: Mus musculus

<400> SEQUENCE: 31

Gln Ser Val Glu Glu Ser Gly Gly Arg Leu Val Thr Pro Glu Thr Pro
1               5                   10                  15

Leu Thr Leu Thr Cys Thr Val Ser Gly Phe Asp Leu Ser Arg Tyr Ala
            20                  25                  30

Met Gly Trp Val Arg Gln Ala Pro Gly Lys Gly Leu Glu Tyr Ile Gly
        35                  40                  45

Leu Ile Val Ser Asp Gly Arg Thr Tyr Tyr Ala Ser Trp Ala Lys Gly
50                  55                  60

Arg Phe Thr Ile Ser Lys Thr Ser Ser Thr Thr Val Asp Leu Lys Met
65                  70                  75                  80

Ala Ser Pro Thr Thr Glu Asp Thr Ala Thr Tyr Tyr Cys Tyr Arg Asn
                85                  90                  95

Val Ser Leu Trp Gly Gln Gly Thr Leu Val Ser Val Ser Glu
            100                 105                 110

<210> SEQ ID NO 32
<211> LENGTH: 27
<212> TYPE: PRT
<213> ORGANISM: artificial sequence
<220> FEATURE:
<223> OTHER INFORMATION: synthetic peptide
<220> FEATURE:
<221> NAME/KEY: Xaa
<222> LOCATION: (1)..(4)
<223> OTHER INFORMATION: Xaa in positions 1, 3 and 4 is beta alanine;
      Xaa in position 2 is 6-aminohexanoic acid

<400> SEQUENCE: 32

Xaa Xaa Xaa Xaa Val Arg Arg Gly Asn Leu Glu Arg Glu Cys Val Glu
1               5                   10                  15

Glu Thr Cys Ser Tyr Glu Glu Ala Phe Glu Ala
            20                  25

<210> SEQ ID NO 33
<211> LENGTH: 20
<212> TYPE: PRT

```
<213> ORGANISM: artificial sequence
<220> FEATURE:
<223> OTHER INFORMATION: synthetic peptide
<220> FEATURE:
<221> NAME/KEY: Xaa
<222> LOCATION: (1)..(4)
<223> OTHER INFORMATION: Xaa in positions 1, 3 and 4 is beta alanine;
      Xaa in position 2 is 6-aminohexanoic acid

<400> SEQUENCE: 33

Xaa Xaa Xaa Xaa Asn Leu Glu Arg Glu Cys Val Glu Glu Thr Cys Ser
1               5                   10                  15

Tyr Glu Glu Ala
            20

<210> SEQ ID NO 34
<211> LENGTH: 20
<212> TYPE: PRT
<213> ORGANISM: artificial sequence
<220> FEATURE:
<223> OTHER INFORMATION: synthetic peptide
<220> FEATURE:
<221> NAME/KEY: Xaa
<222> LOCATION: (17)..(19)
<223> OTHER INFORMATION: Xaa in positions 17 and 19 is beta alanine; Xaa
      in position 18 is 6-aminohexanoic acid

<400> SEQUENCE: 34

Ala Asn Thr Phe Leu Glu Glu Val Arg Lys Gly Asn Leu Glu Arg Glu
1               5                   10                  15

Xaa Xaa Xaa Cys
            20
```